(12) United States Patent
Bleich et al.

(10) Patent No.: US 8,092,456 B2
(45) Date of Patent: Jan. 10, 2012

(54) MULTIPLE PATHWAYS FOR SPINAL NERVE ROOT DECOMPRESSION FROM A SINGLE ACCESS POINT

(75) Inventors: Jeffery L. Bleich, Palo Alto, CA (US); Michael Sheinberg, Diablo, CA (US); Michael P. Wallace, Pleasanton, CA (US)

(73) Assignee: Baxano, Inc., San Jose, CA (US)

( * ) Notice: Subject to any disclaimer, the term of this patent is extended or adjusted under 35 U.S.C. 154(b) by 205 days.

(21) Appl. No.: 12/352,978

(22) Filed: Jan. 13, 2009

(65) Prior Publication Data

US 2009/0177241 A1 Jul. 9, 2009

Related U.S. Application Data

(63) Continuation-in-part of application No. 11/251,205, filed on Oct. 15, 2005, now Pat. No. 7,918,849, and a continuation-in-part of application No. 11/687,548, filed on Mar. 16, 2007.

(60) Provisional application No. 61/106,498, filed on Oct. 17, 2008.

(51) Int. Cl.
*A61B 17/00* (2006.01)
*A61B 17/56* (2006.01)
*A61B 17/58* (2006.01)
*A61B 17/82* (2006.01)
*A61F 2/30* (2006.01)

(52) U.S. Cl. ............... 606/79; 606/74; 606/85

(58) Field of Classification Search .......... 606/74, 606/79, 85

See application file for complete search history.

(56) References Cited

U.S. PATENT DOCUMENTS

| 184,804 A | 11/1876 | Stohlmann |
| 289,104 A | 11/1883 | How |
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |

(Continued)

FOREIGN PATENT DOCUMENTS

DE 3209403 A1 9/1983

(Continued)

OTHER PUBLICATIONS

Barer Malvin, "Instrument to Enhance Passage of the Gigli Saw," Journal of Pediatric Orthopedics, Raven Press, New York, 1984, 4:762-763.

(Continued)

*Primary Examiner* — Thomas C. Barrett
*Assistant Examiner* — David Bates
(74) *Attorney, Agent, or Firm* — Shay Glenn LLP

(57) ABSTRACT

A method of accessing target tissue adjacent to a spinal nerve of a patient includes the steps of accessing a spine location of the patient by entering the patient through the skin at an access location, inserting a flexible tissue modification device through the access location to the spine location, advancing a distal portion of the first flexible tissue modification device from the spine location to a first exit location, passing through the first exit location and out of the patient, advancing the first or a second flexible tissue modification device through the same access location to the spine location and to a second exit location, and passing through the second exit location and out of the patient.

49 Claims, 15 Drawing Sheets

U.S. PATENT DOCUMENTS

| | | |
|---|---|---|
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE025,582 E | 5/1964 | Davies |
| 3,150,470 A | 9/1964 | Barron |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman et al. |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |

| | | | | | | |
|---|---|---|---|---|---|---|
| 5,766,168 | A | 6/1998 | Mantell | 6,277,094 B1 | 8/2001 | Schendel |
| 5,769,865 | A | 6/1998 | Kermode et al. | 6,280,447 B1 | 8/2001 | Marino et al. |
| 5,775,331 | A | 7/1998 | Raymond et al. | 6,292,702 B1 | 9/2001 | King et al. |
| 5,779,642 | A | 7/1998 | Nightengale | 6,298,256 B1 | 10/2001 | Meyer |
| 5,788,653 | A | 8/1998 | Lorenzo | 6,312,392 B1 | 11/2001 | Herzon |
| 5,792,044 | A | 8/1998 | Foley et al. | 6,324,418 B1 | 11/2001 | Crowley et al. |
| 5,795,308 | A | 8/1998 | Russin | 6,324,432 B1 | 11/2001 | Rigaux et al. |
| 5,800,350 | A | 9/1998 | Coppleson et al. | 6,334,068 B1 | 12/2001 | Hacker |
| 5,803,902 | A | 9/1998 | Sienkiewicz et al. | 6,343,226 B1 | 1/2002 | Sunde et al. |
| 5,803,904 | A | 9/1998 | Mehdizadeh | 6,358,254 B1 | 3/2002 | Anderson |
| 5,807,263 | A | 9/1998 | Chance | 6,360,750 B1 | 3/2002 | Gerber et al. |
| 5,810,744 | A | 9/1998 | Chu et al. | 6,364,886 B1 | 4/2002 | Sklar |
| 5,813,405 | A | 9/1998 | Montano, Jr. et al. | 6,368,324 B1 | 4/2002 | Dinger et al. |
| 5,824,040 | A | 10/1998 | Cox et al. | 6,370,411 B1 | 4/2002 | Osadchy et al. |
| 5,830,151 | A | 11/1998 | Hadzic et al. | 6,370,435 B2 | 4/2002 | Panescu et al. |
| 5,830,157 | A | 11/1998 | Foote | 6,383,509 B1 | 5/2002 | Donovan et al. |
| 5,830,188 | A | 11/1998 | Abouleish | 6,390,906 B1 | 5/2002 | Subramanian |
| 5,833,692 | A | 11/1998 | Cesarini et al. | 6,391,028 B1 | 5/2002 | Fanton et al. |
| 5,836,948 | A | 11/1998 | Zucherman et al. | 6,416,505 B1 | 7/2002 | Fleischman et al. |
| 5,843,110 | A | 12/1998 | Dross et al. | 6,423,071 B1 | 7/2002 | Lawson |
| 5,846,196 | A | 12/1998 | Siekmeyer et al. | 6,423,080 B1 | 7/2002 | Gellman et al. |
| 5,846,244 | A | 12/1998 | Cripe | 6,425,859 B1 | 7/2002 | Foley et al. |
| 5,851,191 | A | 12/1998 | Gozani | 6,425,887 B1 | 7/2002 | McGuckin et al. |
| 5,851,209 | A | 12/1998 | Kummer et al. | 6,436,101 B1 | 8/2002 | Hamada |
| 5,851,214 | A | 12/1998 | Larsen et al. | 6,442,848 B1 | 9/2002 | Dean |
| 5,853,373 | A | 12/1998 | Griffith et al. | 6,446,621 B1 | 9/2002 | Svensson |
| 5,865,844 | A | 2/1999 | Plaia et al. | 6,451,335 B1 | 9/2002 | Goldenheim et al. |
| 5,868,767 | A | 2/1999 | Farley et al. | 6,454,767 B2 | 9/2002 | Alleyne |
| 5,879,353 | A | 3/1999 | Terry | 6,464,682 B1 | 10/2002 | Snoke |
| 5,885,219 | A | 3/1999 | Nightengale | 6,466,817 B1 | 10/2002 | Kaula et al. |
| 5,895,417 | A | 4/1999 | Pomeranz et al. | 6,468,289 B1 | 10/2002 | Bonutti |
| 5,897,583 | A | 4/1999 | Meyer et al. | 6,470,209 B2 | 10/2002 | Snoke |
| 5,899,909 | A | 5/1999 | Claren et al. | 6,478,805 B1 | 11/2002 | Marino et al. |
| 5,904,657 | A | 5/1999 | Unsworth et al. | 6,487,439 B1 | 11/2002 | Skladnev et al. |
| 5,916,173 | A | 6/1999 | Kirsner | 6,488,636 B2 | 12/2002 | Bryan et al. |
| 5,918,604 | A | 7/1999 | Whelan | 6,491,646 B1 | 12/2002 | Blackledge |
| 5,919,190 | A | 7/1999 | VanDusseldorp | 6,500,128 B2 | 12/2002 | Marino |
| 5,928,158 | A | 7/1999 | Aristides | 6,500,189 B1 | 12/2002 | Lang et al. |
| 5,928,159 | A | 7/1999 | Eggers et al. | 6,512,958 B1 | 1/2003 | Swoyer et al. |
| 5,941,822 | A | 8/1999 | Skladnev et al. | 6,516,223 B2 | 2/2003 | Hofmann |
| 5,961,522 | A | 10/1999 | Mehdizadeh | 6,520,907 B1 | 2/2003 | Foley et al. |
| 5,972,013 | A | 10/1999 | Schmidt | 6,527,786 B1 | 3/2003 | Davis et al. |
| 5,976,110 | A | 11/1999 | Greengrass et al. | 6,533,749 B1 | 3/2003 | Mitusina et al. |
| 5,976,146 | A | 11/1999 | Ogawa et al. | 6,535,759 B1 | 3/2003 | Epstein et al. |
| 6,002,964 | A | 12/1999 | Feler et al. | 6,540,742 B1 | 4/2003 | Thomas et al. |
| 6,004,326 | A | 12/1999 | Castro et al. | 6,540,761 B2 | 4/2003 | Houser |
| 6,010,493 | A | 1/2000 | Snoke | 6,546,270 B1 | 4/2003 | Goldin et al. |
| 6,015,406 | A | 1/2000 | Goble et al. | 6,558,353 B2 | 5/2003 | Zohmann |
| 6,022,362 | A | 2/2000 | Lee et al. | 6,562,033 B2 | 5/2003 | Shah et al. |
| 6,030,383 | A | 2/2000 | Benderev | 6,564,078 B1 | 5/2003 | Marino et al. |
| 6,030,401 | A | 2/2000 | Marino | 6,564,079 B1 | 5/2003 | Cory et al. |
| 6,038,480 | A | 3/2000 | Hrdlicka et al. | 6,564,088 B1 | 5/2003 | Soller et al. |
| 6,048,345 | A | 4/2000 | Berke et al. | 6,569,160 B1 | 5/2003 | Goldin et al. |
| 6,068,642 | A | 5/2000 | Johnson et al. | 6,575,979 B1 | 6/2003 | Cragg |
| 6,073,051 | A | 6/2000 | Sharkey et al. | 6,579,291 B1 | 6/2003 | Keith et al. |
| 6,099,514 | A | 8/2000 | Sharkey et al. | 6,584,345 B2 | 6/2003 | Govari |
| 6,102,930 | A | 8/2000 | Simmons, Jr. | 6,592,559 B1 | 7/2003 | Pakter et al. |
| 6,106,558 | A | 8/2000 | Picha | 6,595,932 B2 | 7/2003 | Ferrera |
| 6,113,534 | A | 9/2000 | Koros et al. | 6,597,955 B2 | 7/2003 | Panescu et al. |
| D432,384 | S | 10/2000 | Simons | 6,606,523 B1 | 8/2003 | Jenkins |
| 6,132,387 | A | 10/2000 | Gozani et al. | 6,607,530 B1 | 8/2003 | Carl et al. |
| 6,136,014 | A | 10/2000 | Sirimanne et al. | 6,609,018 B2 | 8/2003 | Cory et al. |
| 6,142,993 | A | 11/2000 | Whayne et al. | 6,610,066 B2 | 8/2003 | Dinger et al. |
| 6,142,994 | A | 11/2000 | Swanson et al. | 6,620,129 B2 | 9/2003 | Stecker et al. |
| 6,146,380 | A | 11/2000 | Racz et al. | 6,622,731 B2 | 9/2003 | Daniel et al. |
| 6,152,894 | A | 11/2000 | Kubler | 6,624,510 B1 | 9/2003 | Chan et al. |
| 6,169,916 | B1 | 1/2001 | West | 6,626,916 B1 | 9/2003 | Yeung et al. |
| 6,205,360 | B1 | 3/2001 | Carter et al. | 6,632,184 B1 | 10/2003 | Truwit |
| 6,214,001 | B1 | 4/2001 | Casscells et al. | 6,638,233 B2 | 10/2003 | Corvi et al. |
| 6,214,016 | B1 | 4/2001 | Williams et al. | RE038,335 E | 11/2003 | Aust et al. |
| 6,236,892 | B1 | 5/2001 | Feler | 6,648,883 B2 | 11/2003 | Francischelli et al. |
| 6,251,115 | B1 | 6/2001 | Williams et al. | 6,666,874 B2 | 12/2003 | Heitzmann et al. |
| 6,256,540 | B1 | 7/2001 | Panescu et al. | 6,673,063 B2 | 1/2004 | Brett |
| 6,259,945 | B1 | 7/2001 | Epstein et al. | 6,673,068 B1 | 1/2004 | Berube |
| 6,261,582 | B1 | 7/2001 | Needham et al. | 6,678,552 B2 | 1/2004 | Pearlman |
| 6,266,551 | B1 | 7/2001 | Osadchy et al. | 6,682,535 B2 | 1/2004 | Hoogland |
| 6,266,558 | B1 | 7/2001 | Gozani et al. | 6,682,536 B2 | 1/2004 | Vardi et al. |
| 6,267,760 | B1 | 7/2001 | Swanson | 6,699,246 B2 | 3/2004 | Zucherman et al. |
| 6,272,367 | B1 | 8/2001 | Chance | 6,723,049 B2 | 4/2004 | Skladnev et al. |

| Patent No. | Date | Inventor(s) |
|---|---|---|
| 6,726,531 B1 | 4/2004 | Harrel |
| 6,726,685 B2 | 4/2004 | To et al. |
| 6,733,496 B2 | 5/2004 | Sharkey et al. |
| 6,736,815 B2 | 5/2004 | Ginn |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,772,012 B2 | 8/2004 | Ricart et al. |
| 6,776,765 B2 | 8/2004 | Soukup et al. |
| 6,788,966 B2 | 9/2004 | Kenan et al. |
| 6,790,210 B1 | 9/2004 | Cragg et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,189,240 B1 | 3/2007 | Dekel |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,216,001 B2 | 5/2007 | Hacker et al. |
| 7,223,278 B2 | 5/2007 | Davison et al. |
| 7,239,911 B2 | 7/2007 | Scholz |
| 7,270,658 B2 | 9/2007 | Woloszko et al. |
| 7,282,061 B2 | 10/2007 | Sharkey et al. |
| 7,337,005 B2 | 2/2008 | Kim et al. |
| 7,337,006 B2 | 2/2008 | Kim et al. |
| 7,383,639 B2 | 6/2008 | Malandain |
| 7,470,236 B1 | 12/2008 | Kelleher et al. |
| 7,494,473 B2 | 2/2009 | Eggers et al. |
| 7,503,920 B2 | 3/2009 | Siegal |
| 7,507,218 B2 | 3/2009 | Aliski et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1 | 2/2002 | Erickson et al. |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0183647 A1 | 12/2002 | Gozani et al. |
| 2003/0023190 A1 | 1/2003 | Cox |
| 2003/0045808 A1 | 3/2003 | Kaula et al. |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |
| 2004/0122459 A1 | 6/2004 | Harp |
| 2004/0122482 A1 | 6/2004 | Tung et al. |
| 2004/0127893 A1 | 7/2004 | Hovda |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0199166 A1 | 10/2004 | Schmieding et al. |
| 2004/0260358 A1 | 12/2004 | Vaughan et al. |
| 2005/0027199 A1 | 2/2005 | Clarke |
| 2005/0033393 A1 | 2/2005 | Daglow |

| | | |
|---|---|---|
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0277942 A1 | 12/2005 | Kullas et al. |
| 2005/0283148 A1 | 12/2005 | Janssen et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089609 A1 | 4/2006 | Bleich et al. |
| 2006/0089633 A1 | 4/2006 | Bleich et al. |
| 2006/0089640 A1 | 4/2006 | Bleich et al. |
| 2006/0089650 A1 | 4/2006 | Nolde |
| 2006/0089688 A1 | 4/2006 | Panescu |
| 2006/0094976 A1 | 5/2006 | Bleich |
| 2006/0095026 A1 | 5/2006 | Ricart et al. |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0135882 A1 | 6/2006 | Bleich |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1 | 10/2006 | Bleich et al. |
| 2006/0258951 A1 | 11/2006 | Bleich et al. |
| 2006/0264952 A1 | 11/2006 | Nelson et al. |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen, III et al. |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0255162 A1 | 11/2007 | Abboud et al. |
| 2007/0255369 A1 | 11/2007 | Bonde et al. |
| 2007/0260252 A1 | 11/2007 | Schmitz et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0033465 A1 | 2/2008 | Schmitz et al. |
| 2008/0051812 A1 | 2/2008 | Schmitz et al. |
| 2008/0058874 A1 | 3/2008 | Westlund et al. |
| 2008/0086034 A1 | 4/2008 | Schmitz et al. |
| 2008/0086114 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0197024 A1 | 8/2008 | Simpson et al. |
| 2008/0200912 A1 | 8/2008 | Long et al. |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0275458 A1 | 11/2008 | Bleich et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0054804 A1 | 2/2009 | Gharib et al. |
| 2009/0054936 A1 | 2/2009 | Eggen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0105604 A1 | 4/2009 | Bertagnoli et al. |
| 2009/0105788 A1 | 4/2009 | Bartol et al. |
| 2009/0118709 A1 | 5/2009 | Sand et al. |
| 2009/0124934 A1 | 5/2009 | Rabbitte et al. |
| 2009/0125036 A1 | 5/2009 | Bleich |
| 2009/0138056 A1 | 5/2009 | Anderson et al. |
| 2009/0143807 A1 | 6/2009 | Sand |
| 2009/0143829 A1 | 6/2009 | Shluzas |
| 2009/0177112 A1 | 7/2009 | Gharib et al. |
| 2009/0177144 A1 | 7/2009 | Masmanidis et al. |
| 2009/0182382 A1 | 7/2009 | Justis et al. |
| 2009/0209879 A1 | 8/2009 | Kaula et al. |
| 2009/0216284 A1 | 8/2009 | Chin et al. |
| 2009/0299166 A1 | 12/2009 | Nishida et al. |
| 2010/0057087 A1 | 3/2010 | Cha |
| 2010/0094231 A1 | 4/2010 | Bleich et al. |

| | | | |
|---|---|---|---|
| 2010/0274250 | A1 | 10/2010 | Wallace et al. |
| 2010/0331883 | A1 | 12/2010 | Schmitz et al. |
| 2010/0331900 | A1 | 12/2010 | Garabedian et al. |
| 2011/0004207 | A1 | 1/2011 | Wallace et al. |
| 2011/0046613 | A1 | 2/2011 | Schmitz et al. |
| 2011/0060314 | A1 | 3/2011 | Wallace et al. |
| 2011/0112539 | A1 | 5/2011 | Wallace et al. |
| 2011/0160731 | A1 | 6/2011 | Bleich et al. |
| 2011/0190772 | A1 | 8/2011 | Saadat |
| 2011/0196257 | A1 | 8/2011 | Schmitz et al. |

FOREIGN PATENT DOCUMENTS

| | | |
|---|---|---|
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| JP | 2960140 B2 | 10/1999 |
| JP | 24065380 A2 | 3/2004 |
| RU | 2107459 | 3/1998 |
| WO | WO-96/22057 | 7/1996 |
| WO | WO97/34536 A2 | 9/1997 |
| WO | WO99/18866 A1 | 4/1999 |
| WO | WO99/21500 A1 | 5/1999 |
| WO | WO00/67651 A1 | 11/2000 |
| WO | WO01/08571 A1 | 2/2001 |
| WO | WO 0108571 A1 * | 2/2001 |
| WO | WO01/62168 A2 | 8/2001 |
| WO | WO02/07901 A1 | 1/2002 |
| WO | WO02/34120 A2 | 5/2002 |
| WO | WO02/076311 A2 | 10/2002 |
| WO | WO03/026482 A2 | 4/2003 |
| WO | WO03/066147 A1 | 8/2003 |
| WO | WO2004/002331 A1 | 1/2004 |
| WO | WO2004/028351 A2 | 4/2004 |
| WO | WO2004/043272 A1 | 5/2004 |
| WO | WO2004/056267 A1 | 7/2004 |
| WO | WO2004/078066 A2 | 9/2004 |
| WO | WO2004/080316 A1 | 9/2004 |
| WO | WO2004/096080 A2 | 11/2004 |
| WO | WO2005/009300 A1 | 2/2005 |
| WO | WO2005/057467 A2 | 6/2005 |
| WO | WO2005/077282 A1 | 8/2005 |
| WO | WO2005/089433 A2 | 9/2005 |
| WO | WO2006/009705 A2 | 1/2006 |
| WO | WO2006/015302 A1 | 2/2006 |
| WO | WO2006/017507 A2 | 2/2006 |
| WO | WO2006/039279 A2 | 4/2006 |
| WO | WO2006/042206 A2 | 4/2006 |
| WO | WO2006/044727 A2 | 4/2006 |
| WO | WO2006/047598 A1 | 5/2006 |
| WO | WO2006/058079 A3 | 6/2006 |
| WO | WO2006/058195 A2 | 6/2006 |
| WO | WO2006/062555 A2 | 6/2006 |
| WO | WO2006/086241 A2 | 8/2006 |
| WO | WO2006/099285 A2 | 9/2006 |
| WO | WO2006/102085 A2 | 9/2006 |
| WO | WO2007/008709 A2 | 1/2007 |
| WO | WO2007/021588 A1 | 2/2007 |
| WO | WO2007/022194 A2 | 2/2007 |
| WO | WO2007/059343 A2 | 2/2007 |
| WO | WO2007/067632 A2 | 6/2007 |
| WO | WO2008/008898 A2 | 1/2008 |
| WO | WO2009/012265 A2 | 1/2009 |
| WO | WO2009/018220 A1 | 2/2009 |
| WO | WO2009/021116 A2 | 2/2009 |
| WO | WO2009/036156 A1 | 3/2009 |
| WO | WO2009/046046 A1 | 4/2009 |
| WO | WO2009/058566 A1 | 5/2009 |
| WO | WO2009/151926 A2 | 12/2009 |
| WO | WO-2010/014538 | 4/2010 |

OTHER PUBLICATIONS

Baumgart et al., "Indikation and Technik der Knochendurchtrennung," Der Chirurg, 1998, vol. 69:1188-1196. (in German with Eng Summary).

Bohinski et al., "Novel use of a threadwire saw for high sacral amputation," Journal of neurosurgery: Spine, 2005, vol. 3, 71R78.

Brunori et al., "Celebrating the centennial (1894-1994): Leonardo Gigli and his wire saw," J. Neurosurg, 1995, 82:1086-1090.

Burrows, Harold, "Surgical instruments and appliances used in operations," Faber and Faber, London, 1937, total pp. 4.

Codman Laminectomy Shaver (a Johnson & Johnson company www. codman.com) catalogue, pp. 416-431, [online] Retrieved from the internet: <URL: http:llwww.codman.com/PDFs/Catalog_04_R. pdf>.

Dammann, Gordon, Pictorial Encyclopedia of Civil War Medical Instruments and Equipment, Pictorial Histories Publishing Company, Missoula, Montana, 1983, Total pp. 2.

Edwards et al; "T-Saw Laminoplasty for the Management of Cervical Spondylotic Myelopathy," SPINE, Lippincott Williams & Wilkins, Inc., 2000, vol. 25 (14): 1788R1794.

Ellman Int. Disc-FX System Accessories K052241 [online] Retrieved from the Internet: <URL: http://www.ellman.com/ medical/ >.

Eralp et al., "A comparison of two osteotomy techniques for tibial lengthening," Archives of orthopaedic and trauma surgery, 2004, vol. 124:298R300.

Fessler Richard G, "Minimally Invasive Microendoscopic Decompressive Laminotomy for Lumbar Stenosis," American Association of Neurological Surgeons, 2006, Online CME course, Retrieved on Jun. 29, 2006 from the internt http://www.aans. emedtrain.com/lumbar_stenosis/lumbarStenosis.swf.

Fujita et al., "Chordoma in the Cervical Spine Managed with En Bloc Excision," SPINE, Lippincott Williams & Wilkins, Inc., 1999, 24 (17), 1848-1851.

Goel, Atul, "Neurosurgical forum, Supraorbital Craniotomy," Journal of Neurosurgery, 1994, vol. 81, 642-643.

Gore Smoother User Manual, W. L. Gore & Associates, Inc. Flagstaff, AZ, Dec. 1999,Total pp. 3.

Hara et al., "En Bloc Laminoplasty Performed with Threadwire Saw: Technical Note," Neurosurgery, Jan. 2001, vol. 48, No. 1, pp. 235-239.

Hata et al; "A less invasive surgery for rotator cuff tear: Mini-open repair," Journal of Shoulder and Elbow Surgery, 2001, vol. 10 No. 1, 11-16.

Honl et al; "The Use of Water-Jetting Technology in Prostheses Revision Surgery R First Results of Parameter Studies on Bone and Bone Cement," J. Biomed Mater Res (Applied Biomaterials), John Wiley & Sons, Inc, 2000, 53, 6: 781-790.

Integra Ruggles TM Kerrison Rongeurs [online] Retrieved from the internet: <URL: http://www.integra-ls.com/product!? product=22>.

Jun, Byung-Yoon, "Posterior Lumbar Interbody Fusion With Restoration of Lamina and Facet Fusion," SPINE, Lippincott Williams & Wilkins, Inc., 2000, vol. 25 No. 8, 917R922.

Kawahara et al., "Recapping T-Saw Laminoplasty for Spinal Cord Tumors," SPINE, 1999, vol. 24 No. 13, pp. 1363-1370.

Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680R684.

Miyamoto et al., "Kyphectomy Using a Surgical Threadwire (T-saw) for Kyphotic Deformity in a Child With Myelomeningocele," SPINE, Lippincott Williams & Wilkins, Inc., 2003, vol. 28 No. 10, E187RE190.

Abdel-Wanis et al., "Tumor growth potential after tumoral and instrumental contamination: an in-vivo comparative study of T-saw, Gigli saw, and scalpel," Journal of orthopaedic science, 2001, vol. 6, 424R429.

Mopec Bone-Cutting tool, Product brochure, Total pp. 4.

Nakagiri et al., "Thoracoscopic Rib Resection Using a Gigli Saw," The Annals of Thoracic Surgery, 2005, vol. 80, 755R756.

Osaka et al., "Clinical significance of a wide excision policy for sacrococcygeal chordoma," J Cancer Res Clin Oncol, 2005, Total pp. 6.

Paley et al., "Percutaneous Osteotomies," Orthopedic Clinics of North America, 1991, vol. 22 No. 4, 613-624.
Pancoast, Joseph, "A Treatise on Operative Surgery," Carey and Hart, Philadelphia, 1844, Total pp. 11.
Park et al; "Cases of the Excision of Carious Joints," John Scrymgeour, Glasgow, 1806, Total pp. 6.
Peavy et al., "Comparison of Cortical Bone Ablations by Using Infrared Laser Wavelengths 2.9 to 9.2 µm, Lasers in Surgery and Medicine," 1999, vol. 26, 421R434.
Peltier, Leonard Orthopedics: A History and Iconography, Norman Publishing, San Francisco, 1993, Total pp. 3.
Reckling Frederick, "Modified Stethoscope Earpiece Makes Excellent Gigli Saw Guide," J Bone and Joint Surgery Am, Dec.1972, 54-A(8), 1787-1788.
Rutkow, Ira, "Surgery an Illustrated History," Mosby'Year Book, Inc., St. Louis, 1993, Total pp. 4.
Schwieger et al., "Abrasive Water Jet Cutting as a New Procedure for Cutting Cancellous Bone'in Vitro Testing in Comparison with the Oscillating Saw," Wiley Interscience, www.interscience,wiley.com, Sep. 20, 2004, 223-228.
Sen, Cengiz, Tibia proksimalinde Gigli testeresi ile yapilanperkütan osteotominin güvenilirligi: Kadavra calismasi, Acta orthopaedics et traumatologica turcica, 2002, vol. 36, 136-140; (In Russian w/ Eng Summary).
Shiraishi et al., "Results of Skip Laminectomy-Minimum 2-Year Follow-up Study Compared With Open-Door Laminoplasty," Spine, Lippincott Williams & Wilkins, Inc., 2003, vol. 28 No. 24, 2667-2672.
Shiraishi T., "A new technique for exposure of the cervical spine laminae," Journal of neurosurgery. Spine, 2002, vol. 96(1), 122-126.
Shiraishi T., Skip laminectomy—a new treatment for cervical spondylotic myelopathy, preserving bilateral muscular attachments to the spinous processes: a preliminary report, Spine, 2002, vol. 2(2), 108-115.
Skippen et al., "The Chain Saw R A Scottish Invention," Scottish Medical Journal, 2004, vol. 49(2), 72-75.
Stevens et al., "Calvarial Bone Graft Harvest Using the Gigli Saw," Journal of Oral and Maxillofacial Surgery, 1998, vol. 56, 798-799.
Takada et al., "Unusual Metastasis to the Cauda Equina From Renal Cell Carcinoma," SPINE, Lippincott Williams & Wilkins, Inc., 2003, vol. 28 No. 6, E114RE117.
Paktiss et al., "Afghan Percutaneous Osteotomy," Journal of Pediatric Orthopaedics, Raven Press Ltd, New York, 1993, vol. 13, No. 4, 531-533.
Tomita et al., "Expansive Midline T-Saw Laminoplasty (Modified Spinour Process-Splitting) for the Management of Cervical Myelopathy," Spine, Lippincott Williams & Wilkins, Inc, 1998, 23(1), 32-37.
Tomita et al., "The Threadwire Saw: a New Device for Cutting Bone," The Journal of Bone and Joint Surgery, 1996, vol. 78, 1915-1917.
Tomita et al., "The Use of the T-Saw for Expansive Midline laminoplasty in the Treatment of Cervical Myelopathy," Orthopedics and Traumatology, No. 3, pp. 169-178, 2002.
Tomita et al., "Total en bloc spondylectomy and circumspinal decompression for solitary spinal metastasis," Paraplegia, 1994, 32:36-46.
Tomita K. et al., "Total en bloc spondylectomy for solitary spinal metastases," International Orthopaedics (SICOT), 1994, 18: 291-298.
Truax, Charles, "The Mechanics of Surgery," Chicago, IL; 1899, Total pp. 3.
US Surgical Kerrison Spinal Rongeur K943116 [online] Retrieved from the Internet: <URL: http://www.ussurg.com/uss/index.html>.
Wilkins, Robert H, "Neurosurgical Classics," Johnson Reprint Corporation, New York, 1965, 377-382.
Zeppelin Laminectomy Rongeur K901372, [online] Retrieved from the internet: <URL: http://www.zeppelin-medical.com/download/instruments.pdf>.

Schmitz et al; U.S. Appl. No. 12/060,229 entitled "Method, system, and apparatus for neural localization," filed Mar. 31, 2008.
Schmitz et al.; U.S. Appl. No. 12/324,147 entitled "TiSsue modification devices," filed Nov. 26, 2008.
Schmitz et al.; U.S. Appl. No. 12/352,385 entitled "Devices, methods and systems for neural localization," filed Jan. 12, 2009.
Arcenio et al.; U.S. Appl. No. 12/980,165 entitled "Systems and Methods for Performing Spinal Fusion", filed Dec. 28, 2010.
Bleich et al.; U.S. Appl. No. 12/984,162 entitled "Devices and Methods for Tissue Access", filed Jan. 4, 2011.
Schmitz et al.; U.S. Appl. No. 12/917,253; entitled "Tissue Access Guidewire System and Method"; filed Nov. 1, 2010.
Wallace et al.; U.S. Appl. No. 12/911,537 entitled "Devices and Methods for Treating Tissue", filed Oct. 25, 2010.
Wallace et al.; U.S. Appl. No. 13/007,381 entitled "Tissue Modification Devices", filed Jan. 14, 2011.
Bleich et al.; U.S. Appl. No. 12/428,369 entitled "Devices and methods for tissue modification," filed Apr. 22, 2009.
Garabedian et al.; U.S. Appl. No. 12/824,043; entitled "Surgical Tools for Treatment of Spinal Stenosis"; filed Jun. 25, 2010.
Schmitz et al.; U.S. Appl. No. 12/816,729 entitled Access and Tissue Modification Systems and Methods, filed Jun. 16, 2010.
Wallace et al.; U.S. Appl. No. 12/724,315 entitled "Flexible Neural Localization Devices and Methods," filed Mar. 15, 2010.
Wallace et al.; U.S. Appl. No. 12/773,595 entitled "Tissue Modification Devices and Methods," filed May 4, 2010.
Bleich et al.; U.S. Appl. No. 12/504,545 entitled "Spinal access and neural localization," filed Jul. 16, 2009.
Schmitz et al.; U.S. Appl. No. 12/496,094 entitled "Access and tissue modification systems and methods," filed Jul. 1, 2009.
Saadat et al., U.S. Appl. No. 13/078,376 entitled "Powered Tissue Modification Devices and Methods", filed Apr. 1, 2011.
Schmitz et al.; U.S. Appl. No. 13/090,944 entitled "Method, System and Apparatus for Neutral Localzation", filed Apr. 20, 2011.
US Surgical Kerrison Spinal Rongeur K943116 [online] Retrieved from the internet: <URL: http://www.ussurg.com/uss/index.html>. Jul. 27, 1994.
Zeppelin Laminectomy Rongeur K901372, [online] Retrieved from the internet: <URL: http://www.zeppelin-medical.com/download/instruments.pdf>. Oct. 24, 2006.
Ellman Int. Disc-FX System Accessories K052241 [online] Retrieved from the Internet: <URL: httpp://www.ellman.com/ medical/ >, Feb. 27, 2006.
Schwieger et al., "Abrasive Water Jet Cutting as a New Procedure for Cutting Cancellous Bone—In Vitro Testing in Comparison with the Oscillating Saw," Wiley Interscience, www.interscience.wiley.com, Sep. 20, 2004, 223-228. Sep. 20, 2004.
Mopec Bone-Cutting tool, Product brochure, Total pp. 4. First accessed Dec. 15, 2005.
Codman Laminectomy Shaver (a Johnson & Johnson company www.codman.com) catalogue, pp. 416-431, [online] Retrieved from the internet: <URL: http:llwww.codman.com/PDFs/Catalog_04_R.pdf>. First accessedOct. 24, 2006.
Integra Ruggles TM Kerrison Rongeures [online] Retrieved from the Internet: <URL: http://www.integra-ls.com/products!? product=22<. First accessedOct. 24, 2006.
Bleich et al.; U.S. Appl. No. 13/112,886 entitled "Methods, Systems and Devices for Carpal Tunnel Release", filed May 20, 2011.
Bleich et al.; U.S. Appl. No. 13/112,918 entitled "Methods, Systems and Devices for Carpal Tunnel Release", filed May 20, 2011.
Herkowitz, , "The Cervical Spine Surgery Atlas", Herkowitz, *"The Cervical Spine Surgery Atlas"*, 2004, 2nd Edition Jan. 1, 2004, 203-206, 208.
Bleich et al.; U.S. Appl. No. 13/112,886 entitled "Methods, Systems and Devices for Carpal Tunnel Release", filed May 20, 2011.
Bleich et al.; U.S. Appl. No. 13/112,918 entitled "Methods, Systems and Devices for Carpal Tunnel Release", filed May 20, 2011.

* cited by examiner

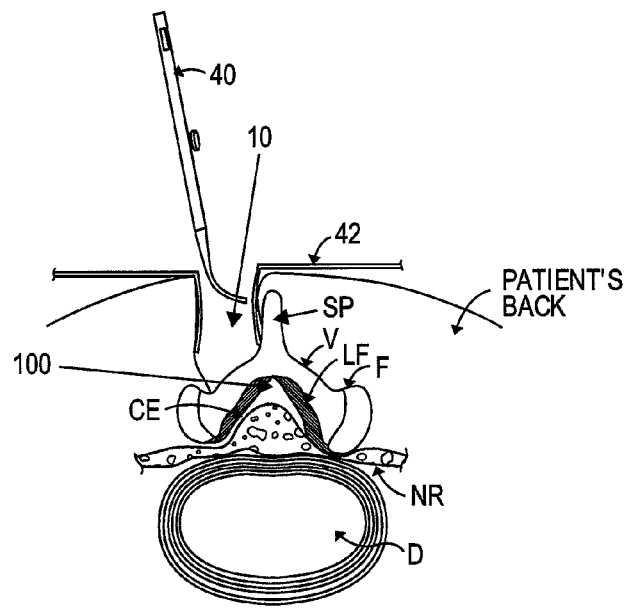
FIG. 4A
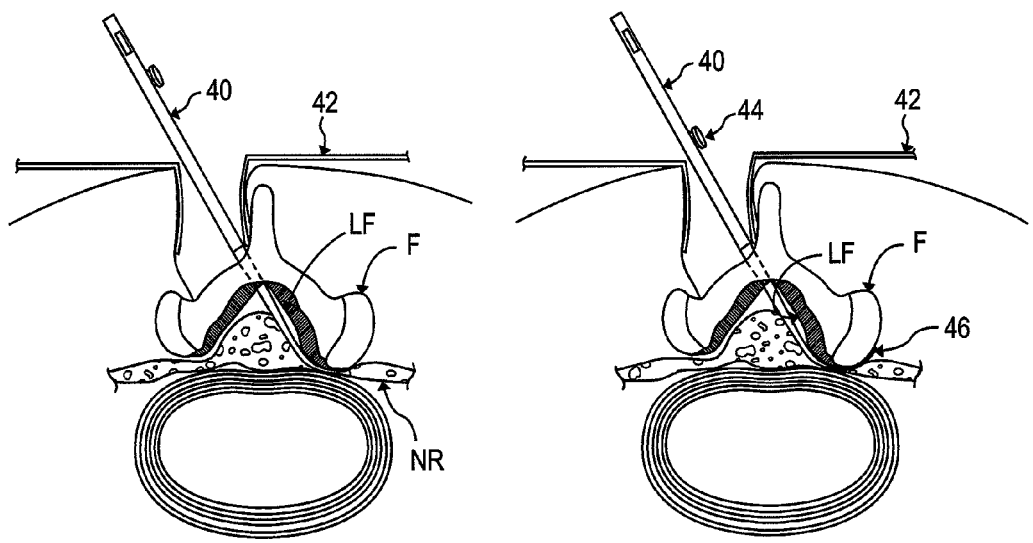
FIG. 4B     FIG. 4C

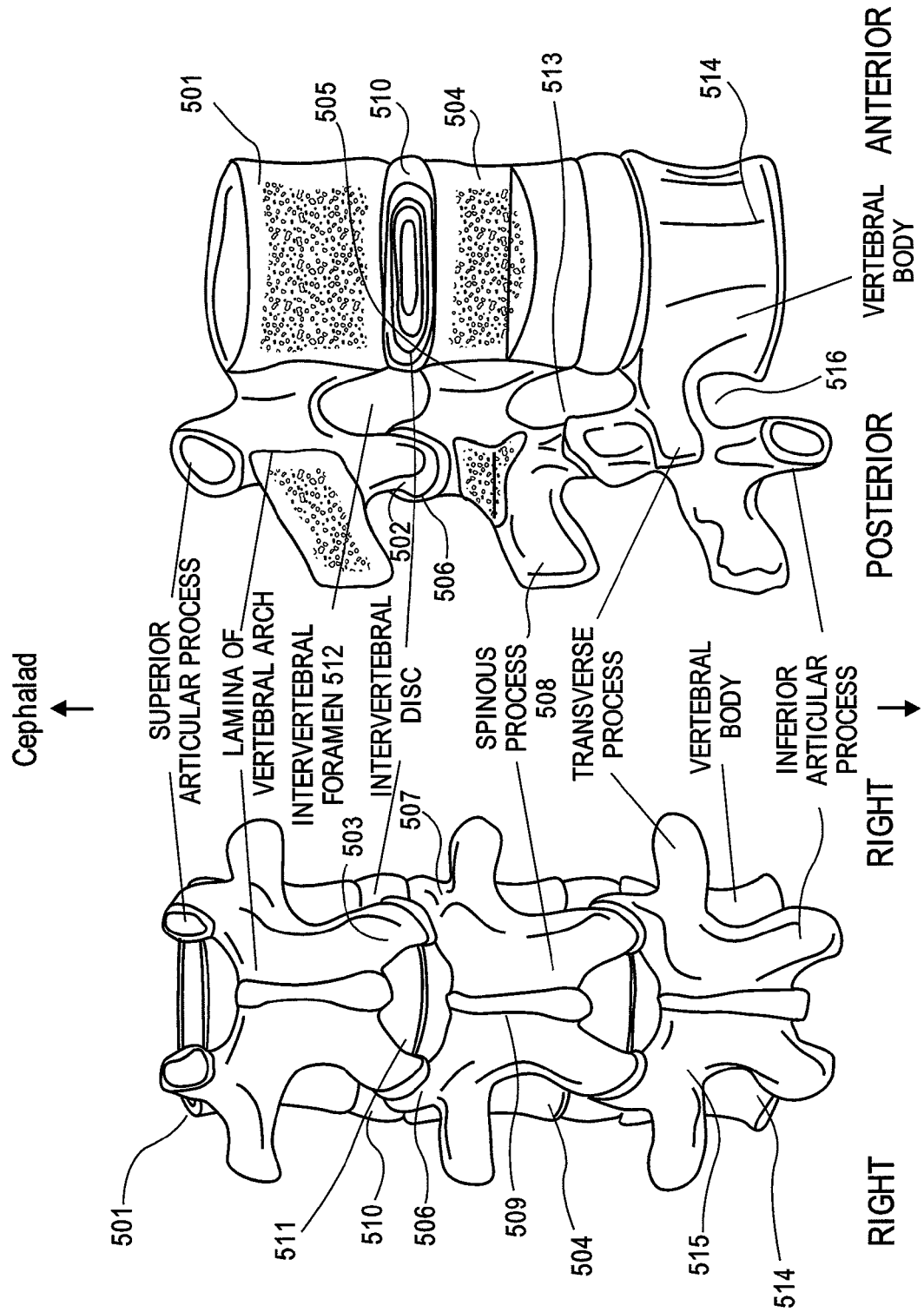

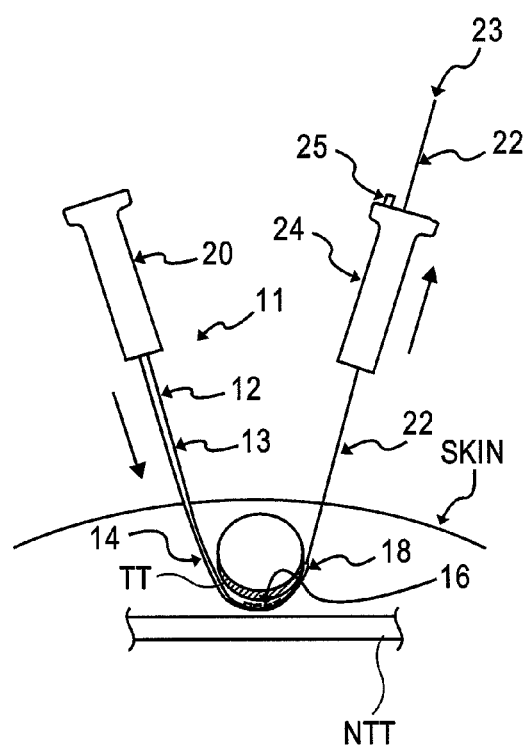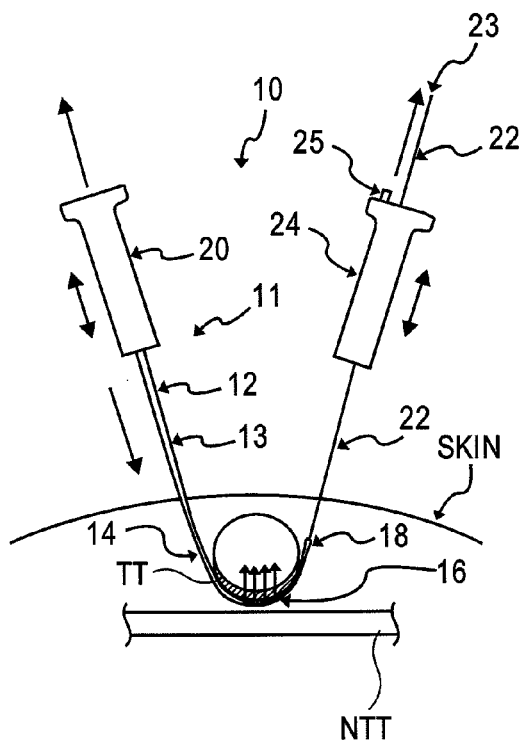
FIG. 9D  FIG. 9E

MULTIPLE PATHWAYS FOR SPINAL NERVE ROOT DECOMPRESSION FROM A SINGLE ACCESS POINT

CROSS-REFERENCE TO RELATED APPLICATIONS

This application claims priority to U.S. Provisional Application No. 61/106,498, titled "MULTIPLE PATHWAYS FOR SPINAL NERVE ROOT DECOMPRESSION FROM A SINGLE ACCESS POINT" filed Oct. 17, 2008, which is incorporated by reference herein in its entirety.

This application is a Continuation-in-Part to U.S. application Ser. No. 11/251,205, titled "Devices and Methods for Tissue Access", filed Oct. 15, 2005 and to U.S. application Ser. No. 11/687,548, titled "Tissue Removal with at Least Partially Flexible Devices", filed Mar. 16, 2007; each of which is incorporated by reference herein in its entirety.

In addition, the methods described herein may be applied to many of the devices and systems described in any of the reference listed below. In particular, these references described flexible (or partially flexible) tissue modification device that may be manipulated bi-manually (e.g., by applying force from both ends of the device). This application may be related to U.S. application Ser. No. 11/250,332, filed Oct. 15, 2005; U.S. application Ser. No. 11/250,369, filed Oct. 15, 2005; U.S. application Ser. No. 11/251,155, filed Oct. 15, 2005; U.S. application Ser. No. 11/251,205, filed Oct. 15, 2005; U.S. application Ser. No. 11/250,902, filed Oct. 15, 2005; U.S. application Ser. No. 11/251,186, filed Oct. 15, 2005; U.S. application Ser. No. 11/251,165, filed Oct. 15, 2005; U.S. application Ser. No. 11/251,204, filed Oct. 15, 2005; U.S. application Ser. No. 11/251,199, filed Oct. 15, 2005; U.S. application Ser. No. 11/952,934, filed Dec. 7, 2007; U.S. application Ser. No. 11/405,848, filed Apr. 17, 2006; U.S. application Ser. No. 11/406,486, filed Apr. 17, 2006; U.S. application Ser. No. 11/405,859, filed Apr. 17, 2006; U.S. application Ser. No. 11/429,377, filed May 4, 2006; U.S. application Ser. No. 11/457,416, filed Jul. 13, 2006; U.S. application Ser. No. 11/687,548, filed Mar. 16, 2007; U.S. application Ser. No. 11/687,558, filed Mar. 16, 2007; U.S. application Ser. No. 11/375,265, filed Mar. 13, 2006; U.S. application Ser. No. 11/461,740, filed Aug. 1, 2006; U.S. application Ser. No. 11/535,000, filed Sep. 25, 2006; U.S. application Ser. No. 11/468,247, filed Aug. 29, 2006; U.S. application Ser. No. 12/127,535, filed May 27, 2008; U.S. application Ser. No. 11/468,252, filed Aug. 29, 2006; U.S. application Ser. No. 11/843,561, filed Aug. 22, 2007; U.S. application Ser. No. 11/538,345, filed Oct. 3, 2006; U.S. application Ser. No. 11/870,370, filed Dec. 10, 2007; U.S. application Ser. No. 12/140,201, filed Jun. 16, 2008; U.S. application Ser. No. 12/170,392, filed Jul. 9, 2008; U.S. application Ser. No. 12/060,229, filed Mar. 31, 2008; U.S. Provisional Application 61/017,512, filed Dec. 28, 2007; U.S. Provisional Application 61/020,670, filed Jan. 11, 2008; U.S. Provisional Application 61/041,215, filed Mar. 31, 2008; U.S. Provisional Application 61/048,448, filed Apr. 28, 2008; U.S. Provisional Application 61/053,761, filed May 16, 2008; U.S. Provisional Application 61/077,441, filed Jul. 1, 2008; U.S. Provisional Application 61/080,647, filed Jul. 14, 2008; U.S. Provisional Application 61/081,685, filed Jul. 17, 2008; U.S. Provisional Application 61/095,568, filed Sep. 9, 2008; U.S. Provisional Application 61/100,145, filed Sep. 25, 2008; each of which is incorporated by reference herein in its entirety.

INCORPORATION BY REFERENCE

All publications and patent applications mentioned in this specification are herein incorporated by reference in their entirety as if each individual publication or patent application was specifically and individually indicated to be incorporated by reference.

FIELD OF THE INVENTION

The present invention relates generally to medical/surgical devices and methods. More specifically, the present invention relates to methods of accessing and modifying tissue, particularly methods of accessing and modifying tissue with flexible tissue modification devices for treatment of spinal stenosis.

BACKGROUND OF THE INVENTION

A significant number of surgical procedures involve modifying tissue in a patient's body, such as by removing, cutting, shaving, abrading, shrinking, ablating or otherwise modifying tissue. Minimally invasive (or "less invasive") surgical procedures often involve modifying tissue through one or more small incisions or percutaneous access, and thus may be more technically challenging procedures. Some of the challenges of minimally invasive tissue modification procedures include working in a smaller operating field, working with smaller devices, and trying to operate with reduced or even no direct visualization of the tissue (or tissues) being modified. For example, using arthroscopic surgical techniques for repairing joints such as the knee or the shoulder, it may be quite challenging to modify certain tissues to achieve a desired result, due to the required small size of arthioscopic instruments, the confined surgical space of the joint, lack of direct visualization of the surgical space, and the like. It may be particularly challenging in some surgical procedures, for example, to cut or contour bone or ligamentous tissue with currently available minimally invasive tools and techniques. For example, trying to shave a thin slice of bone off a curved bony surface, using a small-diameter tool in a confined space with little or no ability to see the surface being cut, as may be required in some procedures, may be incredibly challenging or even impossible using currently available devices.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina (FIG. 2) on either side of the vertebra.

FIG. 2 illustrates the spine in sagittal section. The spine comprises multiple vertebrae each having spinous process, facet joint, and intervertebral foramen. Pedicles form inferior and superior boundaries of the intervertebral foramen and are connected to the spinous process by lamina (FIG. 1). Interspinal ligaments extend between adjacent spinous processes, while ligamentum flavum (FIG. 1) connect adjacent lamina and are separated from dura mater and spinal cord (not shown) by epidural space (FIG. 1). Dura mater encapsulates the spinal cord as it runs down the spinal canal, as well as nerve roots as they exit through the lateral recesses and neural foramen. Vertebral bodies and intervertebral discs are disposed anterior of the spinal cord.

Spinal stenosis can occur when the spinal cord, cauda equina and/or nerve root(s) are impinged by one or more tissues in the spine, such as buckled or thickened ligamentum flavum, hypertrophied facet joint (shown as superior articular processes in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% (or more) of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Furthermore, it is often difficult to access an entire impinged nerve root to remove all impinging tissue along the length of the nerve root. This may require a surgeon to remove additional healthy tissue to create multiple access locations. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the affected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods for accessing and modifying target tissue in a spine to help ameliorate or treat spinal stenosis, while inhibiting unwanted damage to non-target tissues. Ideally, such techniques and devices would reduce neural and/or neurovascular impingement without removing significant amounts of vertebral bone, joint, or other spinal support structures, thereby avoiding the need for spinal fusion and, ideally, reducing the long-term morbidity resulting from currently available surgical treatments. Furthermore, such methods would minimize the need to dissect through a wide incision or multiple small incisions on the back that typically causes extensive muscle damage. It may also be advantageous to have minimally invasive or less invasive methods and tissue modification devices capable of treating target tissues in parts of the body other than the spine.

SUMMARY OF THE INVENTION

Any of the methods and devices described herein may be used as part of a tissue decompression (e.g., spinal decompression) method to modify tissue such as soft tissue (e.g., ligamenum flavum, etc.) and hard tissue (e.g., bone). In particular, these methods and devices may be used as part of a spinal decompression technique within a spinal foramen.

Described herein are methods of accessing target tissue adjacent to a spinal nerve of a patient. In some embodiments, the method includes the steps of accessing a spine location of the patient through the skin at an access location that is anterior to the posterior aspect of the ligamentum flavum and posterior to the dura mater of the spinal cord and cauda equina; inserting a first flexible tissue modification device through the access location to the spine location; advancing a distal portion of the first flexible tissue modification device from the spine location to a first exit location; passing through the first exit location and out of the patient; advancing the first or a second flexible tissue modification device through the same access location to the spine location and to a second exit location; and passing through the second exit location and out of the patient.

In some embodiments, the method further comprises the steps of removing the first flexible tissue modification device from the patient and/or removing the second flexible tissue modification device from the patient. In some embodiments, the method further comprises the steps of inserting the first, the second, or a third flexible device through the same access location to the spine location; and advancing the first, the second or the third flexible device from the spine location to a third exit location.

In some embodiments, the step of advancing the first or the second flexible tissue modification device to a first or second exit location comprises advancing the first or the second flexible tissue modification device to a first or second intervertebral foramen. In some embodiments, the step of passing through a first or a second exit location comprises leaving a proximal portion of the first or the second flexible tissue modification in the first or second intervertebral foramen. In some embodiments, the step of advancing the first or a second flexible tissue modification device comprises advancing the first flexible tissue modification device through the same access location to the second exit location.

In some embodiments, the step of accessing a spine location of the patient through an access location comprises accessing a spine location of the patient through an interlaminar window of the patient. In some embodiments, the step of accessing a spine location of the patient through an interlaminar window is achieved without removing a portion of the patient's lamina. In some embodiments, the step of accessing a spine location of the patient through an access location comprises advancing an access device through the access location to the spine location.

In some embodiments, the step of advancing the access device through the access location to the spine location comprises advancing the access device into a midline portion of the back of the patient, lateral to a spinous process, and toward the spine location. In some embodiments, the step of advancing an access device through the access location to the spine location comprises advancing a needle percutaneously through the access location to the spine location. In some embodiments, the step of advancing an access device through the access location to the spine location comprises advancing the access device into a lateral side of the back of the patient, through an intervertebral foramen, and toward the spine location. In some embodiments, the step of advancing the first flexible device from the spine location to the first exit location comprises advancing at least a portion of a probe through the access device from the spine location toward the first exit location, and advancing a guidewire through the probe such that the guidewire is positioned at least partially around a target tissue. In some embodiments, the step of passing through the first or second exit location and out of the patient comprises advancing the guidewire through the first or second exit location and exiting the patient with the guidewire.

In some embodiments, the step of advancing the first flexible device from the spine location to a first exit location comprises advancing the first flexible device from the spine location, anterior to a superior articular process, and through a first intervertebral foramen; and wherein the step of advancing the first or the second flexible device from the spine location to the second exit location comprises advancing the first or second flexible device from the spine location, anterior to a superior articular process, and through a second intervertebral foramen. In some embodiments, the step of advancing the first flexible device from the spine location to a first exit location comprises advancing the first flexible device from the spine location, anterior to a superior articular process, and through a first intervertebral foramen; and wherein the step of advancing the first or the second flexible device from the spine location to the second exit location comprises advancing the first or second flexible device from the spine location, anterior to a superior articular process, and through a second intervertebral foramen. In some embodiments, the step of advancing the first flexible device from the spine location to the first exit location comprises advancing the first flexible device from the spine location, anterior to a superior articular process and cephalad to a pedicle, and through a intervertebral foramen; and wherein the step of advancing the first or second flexible device from the spine location to the second exit location comprises advancing the first or second flexible device from the spine location, anterior to a lamina and caudal to the pedicle, and through a second intervertebral foramen.

In some embodiments, the step of advancing the first or second flexible device from the spine location to the first or second exit location comprises positioning the first or second flexible device at least partially around a target tissue, and in some embodiments, the step of positioning the first or second flexible device at least partially around the target tissue comprises positioning the first or second flexible device anterior to a superior articular process and posterior to neuronal tissue. In some embodiments, the step of positioning the first or second flexible device at least partially around the target tissue comprises positioning the flexible device within a portion of a ligamentum flavum.

In some embodiments, the method further comprises the step of moving the first or second flexible device against the target tissue by pulling the first or second flexible device from at least one of the distal or proximal end of the first or second flexible device. In some embodiments, the step of moving the first or second flexible device against a target tissue by pulling the first or second flexible device from at least one of the distal or proximal end of the device comprises applying tension to both the proximal end and the distal end of the first or second flexible device to drive the flexible device against the target tissue. In some embodiments, the step of applying tension to both the proximal end and the distal end of the first or second flexible device to drive the first or second flexible device against the target tissue comprises applying tension to the distal end of the first or second flexible device using the guidewire. In some embodiments, applying tension to the distal end of the first or second flexible device using the guidewire comprises applying tension to the distal end of the guidewire external to the patient and a proximal end of the guidewire external to the patient.

In some embodiments, the method further comprises the step of modifying the target tissue with the first or second flexible device. In some embodiments, the step of modifying a target tissue with the first or second flexible device comprises modifying the target tissue with a flexible radio-frequency device. In some embodiments, the step of modifying a target tissue with a first or second flexible device comprises modifying the target tissue with a flexible abrasion device. In some embodiments, the step of modifying a target tissue with the flexible device comprises modifying the target tissue with a flexible rongeur device.

In some embodiments, the method further comprises the step of detecting neuronal tissue near the first or second flexible device. In some embodiments, the step of detecting neuronal tissue near the first or second flexible device comprises detecting neuronal tissue with the first or second flexible device.

In some embodiments, the method includes the steps of accessing a spine location of the patient by entering the patient through an access location, wherein the spine location is anterior to the posterior aspect of the ligamentum flavum and posterior to the dura mater of the spinal cord and cauda equina, and the access location is lateral to the spinous process; inserting a first flexible device through the access location, through the interlaminar window, and to the spine location; advancing a distal portion of the first flexible device from the spine location, laterally through a first intervertebral foramen; passing through the first intervertebral foramen and out of the patient; inserting the first or a second flexible device through the same access location, through the interlaminar window, and to the spine location; and advancing a distal portion of the first or second flexible device from the spine location and laterally through a second intervertebral foramen; and passing through the second intervertebral foramen and out of the patient. In some embodiments, the step of inserting the first or second flexible device through the access location, through the interlaminar window, and to the spine location is achieved without removing a portion of the patient's lamina.

In some embodiments, the step of advancing the first flexible device from the spine location and laterally through a first intervertebral foramen comprises advancing the first flexible device anterior to the ipsilateral superior articular process. In some embodiments, the step of advancing the first flexible device from the spine location and laterally through a first intervertebral foramen comprises positioning the first flexible device posterior to and adjacent to a first nerve root, wherein the first nerve root exits through the first intervertebral foramen, wherein the first intervertebral foramen is defined by the same vertebra that define the interlaminar window. In some embodiments, the step of positioning the first flexible device posterior to the first nerve root comprises positioning the first flexible device posterior to and adjacent to the exiting portion of the first nerve root.

In some embodiments, the step of advancing the first or second flexible device from the spine location and laterally through a second intervertebral foramen comprises advancing the first or second flexible device anterior to the lamina. In some embodiments, the step of advancing the first or second flexible device from the spine location and laterally through a second intervertebral foramen comprises positioning the flexible device posterior to and adjacent to a second nerve root, wherein the second nerve root exits through the second intervertebral foramen, wherein the second intervertebral foramen is caudal to the first intervertebral foramen. In some embodiments, the step of positioning the first or second flexible device posterior to the second nerve root comprises positioning the first or second flexible device posterior to and adjacent to the traversing portion of the second nerve root.

In some embodiments, the step of advancing the first flexible device from the spine location and laterally through a first intervertebral foramen comprises advancing the first flexible device anterior to a contralateral superior articular process and through a contralateral intervertebral foramen, wherein the contralateral superior articular process and the contralateral intervertebral foramen are contralateral to the access location. In some embodiments, the step of advancing the first or second flexible device from the spine location, laterally through the second intervertebral foramen comprises advancing the flexible device anterior to the lamina, and through the caudal intervertebral foramen, wherein the lamina and the caudal intervertebral foramen are contralateral to the access location and the caudal intervertebral foramen is caudal to the first intervertebral foramen. In some embodiments, the step of advancing the first or second flexible device from the spine location and laterally through the first or second intervertebral foramen comprises positioning the first or second flexible device at least partially around a target tissue. In some embodiments, the step of positioning the first or second flexible device at least partially around the target tissue comprises positioning the first or second flexible device between within a portion of a ligamentum flavum.

In some embodiments, the method further comprises the steps of modifying the target tissue with the first or second flexible device. In some embodiments, the steps of modifying the target tissue with the first or second flexible device comprises decompressing a nerve root of the patient at multiple locations along the nerve root. In some embodiments, decompressing the nerve root of the patient at multiple locations along the nerve root comprises decompressing the nerve root at least two of a central canal, a lateral recess, and through the first or second intervertebral foramen.

In some alternative embodiments, the method includes the steps of accessing a spine location of the patient by entering the patient through a first access location, wherein the spine location is anterior to the posterior aspect of the ligamentum flavum and posterior to the dura mater of the spinal cord and cauda equina; inserting a first flexible tissue modification device through the first access location to the spine location; advancing a distal portion of the first flexible tissue modification device from the spine location to an exit location; passing through the exit location and out of the patient; inserting the first or a second flexible tissue modification device through a second access location to the spine location; advancing a distal portion of the first or a second flexible tissue modification device from the spine location to the same exit location; and passing through the same exit location and out of the patient. In some embodiments, the step of advancing the first or second flexible tissue modification device from the spine location to the exit location comprises advancing the first or second flexible tissue modification device from the spine location to an interlaminar window.

In some embodiments, the method further comprises the steps of accessing a spine location of the patient through a third access location; inserting the first, the second or a third flexible device through the third access location to the spine location; and advancing the first, second or third flexible device from the spine location to the same exit location.

The methods and devices described herein may be used as part of a guide-based access and decompression system, including those previously described in any of the patent applications and provisional patent applications mentioned in this application.

BRIEF DESCRIPTION OF THE DRAWINGS

FIGS. 4A-4G are cross-sectional views through a patient's spine, illustrating a variation of the method of accessing target tissue adjacent to a spinal nerve of a patient.

FIGS. 6A and 6B are a lateral view and a posterior view of three vertebrae of a patient's spine.

FIGS. 9A-9E are cross-sectional views through a patient's spine, illustrating a variation of the method of accessing target tissue adjacent to a spinal nerve of a patient.

DETAILED DESCRIPTION

Various embodiments of methods for accessing target tissue adjacent to a spinal nerve of a patient as well as tissue modification devices and systems for use in various embodiments of the methods are provided herein. In general, the methods as described herein are for accessing target tissue adjacent to a spinal nerve of a patient. In particular, these methods are for accessing and decompressing a spinal stenosis.

Although much of the following description and accompanying figures generally focuses on surgical procedures in spine, in alternative embodiments, devices, systems and methods of the present invention may be used in any of a number of other anatomical locations in a patient's body. For example, in some embodiments, the methods and devices may be used in minimally invasive procedures in the shoulder, elbow, wrist, hand, hip, knee, foot, ankle, other joints, or other anatomical locations in the body. Similarly, although some embodiments may be used to access and remove or otherwise modify ligamentum flavum and/or bone in a spine to treat spinal stenosis, in alternative embodiments, other tissues may be accessed and modified to treat any of a number of other conditions. For example, in various embodiments, treated tissues may include but are not limited to ligament, tendon, bone, tumor, cyst, cartilage, scar, osteophyte, inflammatory tissue and the like. Non-target tissues may include neural tissue and/or neurovascular tissue in some embodiments or any of a number of other tissues and/or structures in other embodiments. In one alternative embodiment, for example, a flexible tissue modification device may be used to incise a transverse carpal ligament in a wrist while inhibiting damage to the median nerve, to perform a minimally invasive carpal tunnel release procedure. Thus, various embodiments described herein may be used to access and modify any of a number of different tissues, in any of a number of anatomical locations in the body, to treat any of a number of different conditions.

Any of the methods and devices described herein may be used to access and modify tissue, particularly spinal tissue. In particular, these methods and devices may be used to access and decompress a region of the spine, such as the region within a spinal foramen. Any of these devices may be used as part of a bimanual method (see, for example, the incorporated references). Such bimanual devices may include an attachment site for one or more handles (e.g., proximally) and/or one or more guidewires. For example, the distal end of the device may be configured to releasably secure to a guidewire so that the device may be pulled into position within the body (e.g., within a spinal foramen).

Methods for Accessing Target Tissue

Figure 10:
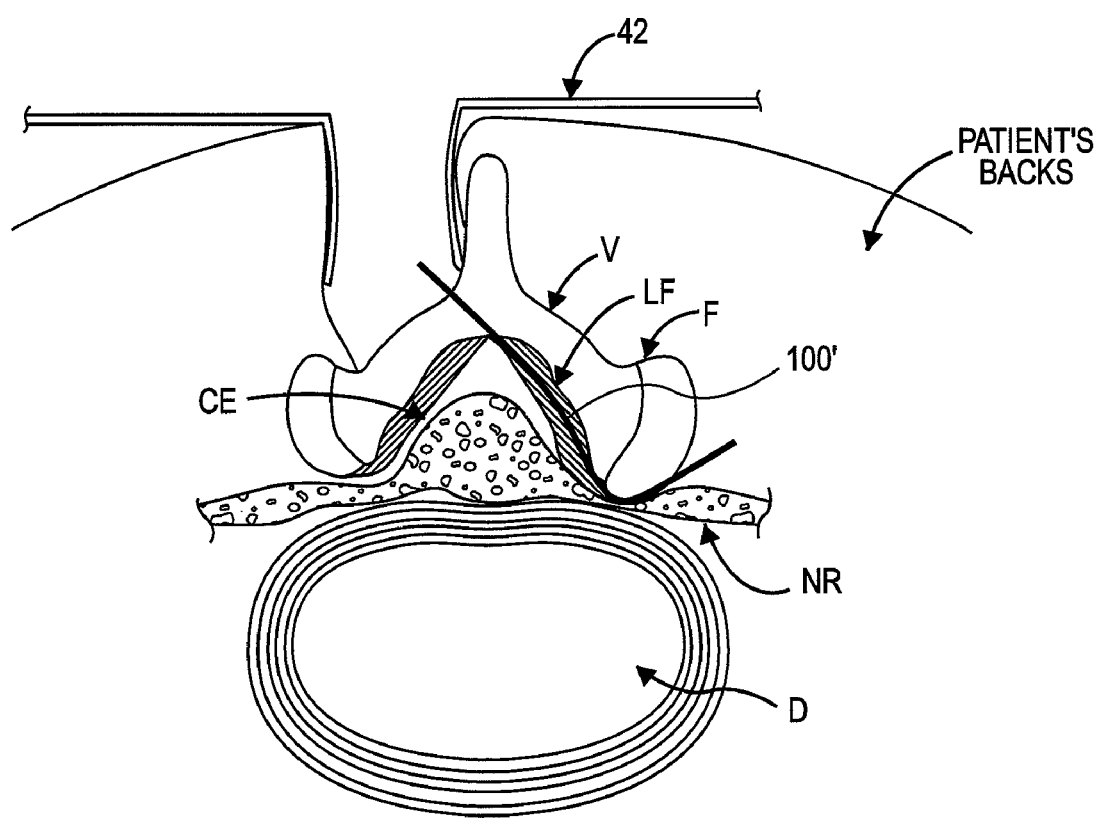
FIG. 10 is a cross-section view through a patient's spine, illustrating a variation of the spine location.

In some embodiments, the method of accessing target tissue adjacent to a spinal nerve of a patient includes the steps of accessing a spine location of the patient by entering the patient through the skin at an access location; inserting a flexible tissue modification device through the access location to the spine location; advancing a distal portion of the first flexible tissue modification device from the spine location to a first exit location; passing through the first exit location and out of the patient; advancing the first or a second flexible tissue modification device through the same access location to the spine location and to a second exit location; and passing through the second exit location and out of the patient. In some embodiments, the spine location is anterior to the posterior aspect of the ligamentum flavum and posterior to the dura mater of the spinal cord and cauda equina. In some embodiments, as shown in FIG. 4A, the spine location 100 is the epidural space. In some embodiments, as shown in FIG. 10, the spine location 100' is within a portion of a ligamentum flavum LF. The methods are designed for accessing target tissue, and more specifically, for accessing and decompressing a spinal stenosis. Furthermore, the methods are designed for decompressing a nerve root of the patient at multiple locations along the nerve root, all from a single access point. The multiple locations along the nerve root may include at least two of a central canal, a lateral recess, and through the first or second intervertebral foramen of the patient. The methods however, may be alternatively used for any other suitable disease, in any suitable environment and for any suitable reason.

FIGS. 6A and 6B illustrate a posterior view and a lateral view, respectively, of a portion of a spine of a patient. The portion of the spine shown includes, labeled from top to bottom, first lumbar vertebra 501, second lumbar vertebra 504, and third lumbar vertebra 514. The first lumbar vertebra includes left inferior articular process 502 and right inferior articular process 503. The second lumbar vertebra includes left pedicle 505, a right pedicle (not shown), left superior articular process 506, right superior articular process 507, spinous process 508, and lamina of vertebral arch 509. Intervertebral disc 510 is disposed between the first lumbar vertebra and the second lumbar vertebra. Interlaminar window 511 is defined by the first lumbar vertebra and the second lumbar vertebra. The third lumbar vertebra includes third lamina of vertebral arch 515. The first lumbar vertebra and the second lumbar vertebra define two intervertebral foramen: left intervertebral foramen 512, cephalad to the left pedicle, and a right intervertebral foramen (not shown), cephalad to the right pedicle. The second lumbar vertebra and the third lumbar vertebra define two intervertebral foramen: caudal left intervertebral foramen 513, caudal to the left pedicle, and a caudal right intervertebral foramen (not shown), caudal to the right pedicle. The third lumbar vertebra and a fourth lumbar vertebra (not shown) define two intervertebral foramen: third left intervertebral foramen 516, and a third right intervertebral foramen (not shown).

The step of accessing a spine location of the patient by entering the patient through the skin at an access location provides access (i.e. creates a channel) from the patient's skin to the spine location such that surgical instruments, drugs, or any other suitable device may access the spine location and/or target tissue. Although this step is shown in reference to placement of a device in a spine, in various alternative embodiments, such a method may be used to place similar or alternative tissue modification devices in other locations in a human body, such as between tissues in a joint space, in the abdominal cavity, or in the carpal tunnel of the wrist, between bone and soft tissue in other parts of the body, and the like.

In some variations, the step of accessing a spine location of the patient through an access location includes the steps of entering the patient's skin, passing through an interlaminar window of the patient's spine, passing through at least a portion of the ligamentum flavum, and entering the spine location. The step of entering the patient's skin may be completed by inserting a needle and/or creating an incision. In some variations, the incision may be widened through the use of surgical instruments, such as retractors for example. In some variations, the step of passing through the interlaminar window of the patient's spine is completed without removing a portion of the patient's lamina. The interlaminar window may be enlarged by use of surgical instruments, such as distractors for example.

FIGS. 4A and 4B illustrate a first variation of the step of accessing the spine location. As shown in FIG. 4A, the step of accessing spine location 100 of the patient may comprise advancing access device 40 through access location 10 to the spine location. The access device may be advanced into a midline portion of the back of the patient, lateral to spinous process SP, and toward the spine location. The access device may be inserted into a patient's back using an open technique facilitated by retractors 42. Alternatively, the access device, such as a probe or an epidural needle, may be inserted into a patient's back using a mini-open or percutaneous technique. Relevant tissues, as shown in FIG. 4A, may include an intervertebral disc (D), ligamentum flavum (LF) and/or facet joint (F) tissue of a vertebra (V), which may impinge on non-target tissues, such as nerve root (NR) and/or cauda equina (CE), of the lumbar spine. The spine location is anterior to the posterior aspect of the ligamentum flavum and posterior to the dura mater of the spinal cord and cauda equina. As shown in FIG.

4B, a curved distal portion of access device 40 may be advanced to the spine location. As shown, the access device may be advanced to a position between target ligamentum flavum (LF) and non-target nerve root (NR) tissues.

Figure 4D:
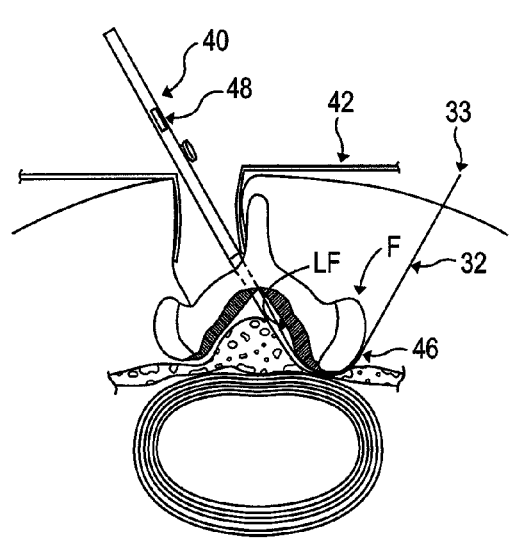
Figure 5A:
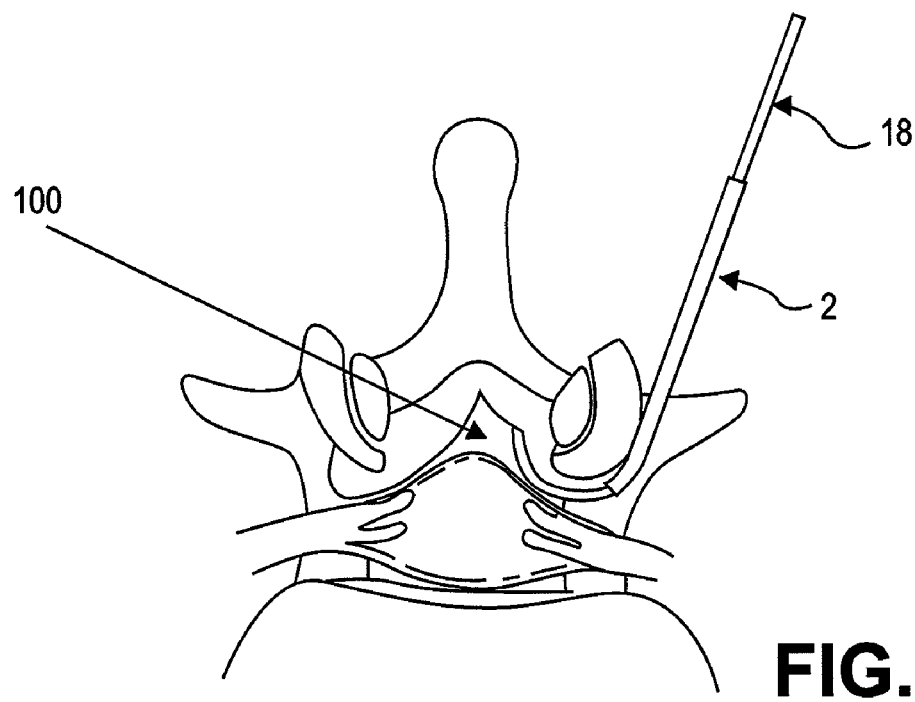
FIGS. 5A and 5B are cross-sectional views through a patient's spine, illustrating a variation of the method of accessing target tissue adjacent to a spinal nerve of a patient

FIG. 5A illustrates a second variation of the step of accessing a spine location. In this variation, the step of advancing an access device through the access location to the spine location may comprise advancing the access device into a lateral side of the back of the patient, through an intervertebral foramen, and toward the spine location. For example, as shown in FIG. 5A, access device 40 may be placed from the lateral side of the patient and through an intervertebral foramen 12'. The access device may be inserted into a patient's back using a mini-open or percutaneous technique. For example, the step of advancing an access device through the access location to the spine location may comprise advancing a needle (such as an epidural needle) percutaneously through the access location to the spine location. Alternatively, the access device, such as a probe, may be inserted into a patient's back using an open technique facilitated by retractors. As shown in FIG. 5A, the access device may include steerable cannula 18 that may be advanced through access element 2 from the lateral towards the medial side of the intervertebral foramen toward spine location 100. Alternatively, a guidewire may be advanced through the cannula to access the spine location or the access device may have a curved end to access the spine location, as shown in FIG. 4A.

Figure 7A:
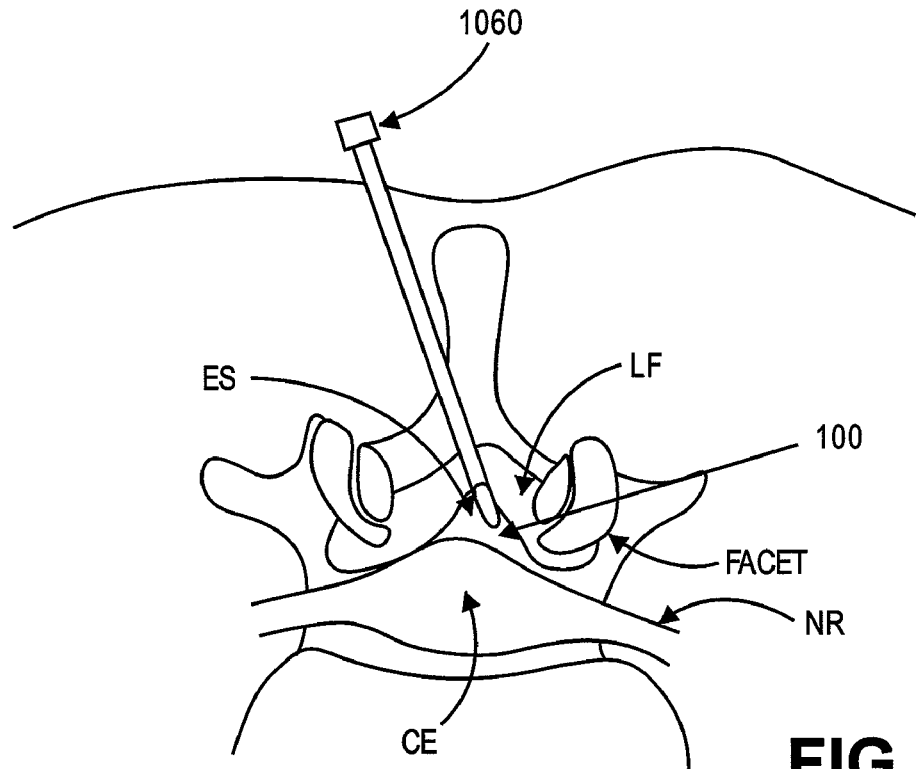
FIGS. 7A-7D are cross-sectional views through a patient's spine, illustrating a variation of the method of accessing target tissue adjacent to a spinal nerve of a patient.
Figure 7B:
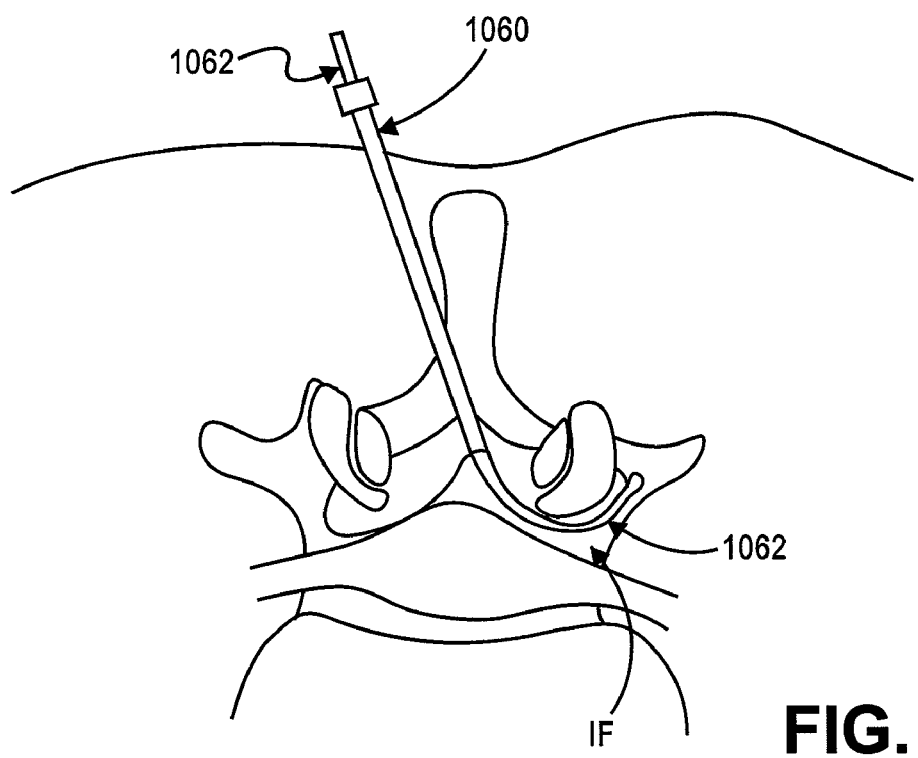

FIG. 7A illustrates a third variation of the step of accessing a spine location. As shown in FIG. 7A, an access device, such as epidural needle 1060 (or cannula), may be passed through the patient's skin, and a distal tip of needle 1060 may be advanced through the ligamentum flavum LF of the spine into the spine location. In some variations, as shown in FIG. 7A, the spine location is the epidural space ES.

Figure 4E:
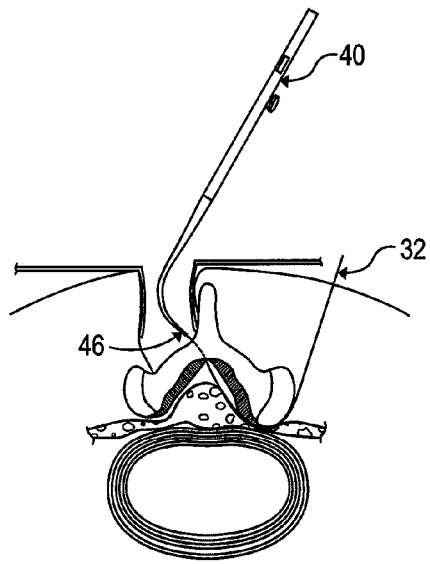
Figure 4F:
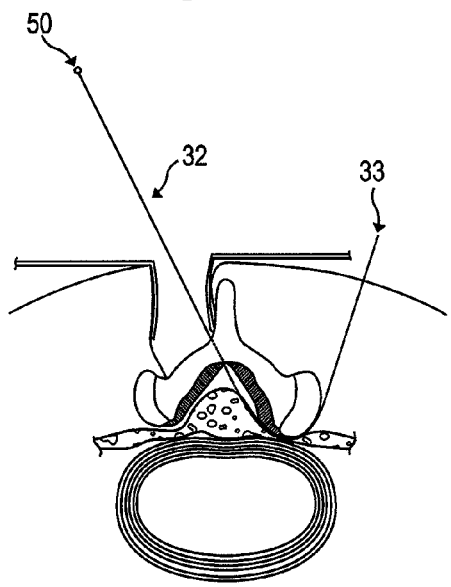
Figure 4G:
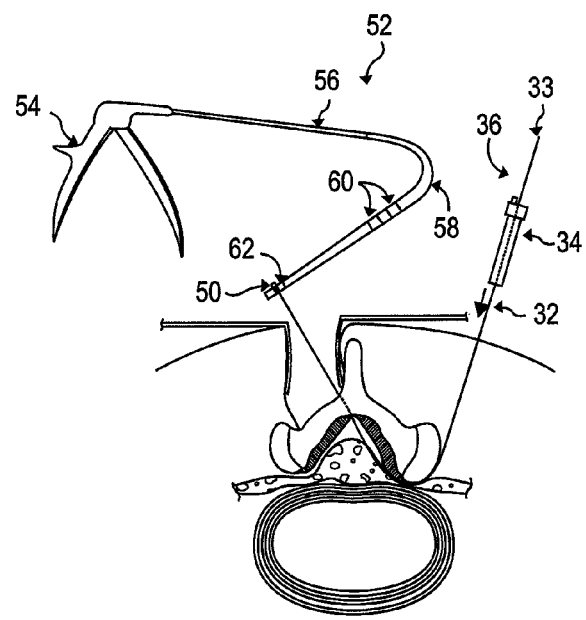

The step of inserting a flexible tissue modification device through the access location to the spine location positions a tissue modification device such that it may be utilized to modify a target tissue. The flexible tissue modification device may be passed through the channel created from the access location to the spine location. FIG. 4G illustrates a first variation of the step of inserting a flexible tissue modification device through the access location to the spine location. In this variation, the step of inserting a flexible tissue modification device through the access location to the spine location comprises pulling flexible tissue modification device 52 through the access location 10 and to the spine location 100 by pulling on guidewire 32, which is coupled to a distal portion of the tissue modification device. In this variation, once guidewire 32 is positioned in a desired location, its proximal end with shaped member 50 may be coupled with a coupling member 62 on a distal end of a tissue modification device. Tissue modification device, in one embodiment, may include a proximal handle 54, a rigid proximal shaft portion 56, a flexible distal shaft portion 58, tissue cutting blades 60, and coupling member 62. The coupling member may be either attached to or formed in distal shaft portion 58 of the tissue modification device. In some embodiments, such as the one depicted in FIG. 4G, to attach the guidewire to a coupling member, the guidewire may be laid into a channel on coupling member, and the guidewire and/or distal portion may be rotated, relative to one another, to lock the shaped member into coupling member. Before, after or during coupling of the guidewire and tissue modification device, the guidewire may also be coupled with distal guidewire handle 34, such as by advancing distal handle over the guidewire (solid-tipped arrow). Once the guidewire is coupled to the tissue modification device, the distal end of the guidewire and/or the distal handle may be pulled, thereby pulling the tissue modification device along the path of the guidewire, through the access location and to the spine location.

In a second variation, the tissue modification device may be inserted through the access location to the spine location by pushing or pulling the modification device over a guidewire to the spine location. In this variation, the guidewire may function as a track or rail that the tissue modification device may be pushed or pulled over. In a third variation, the flexible tissue modification device may be inserted through the access location to the spine location without the use of a guidewire. In this variation, the tissue modification device may be pushed to the spine location by pushing on a proximal handle and/or proximal end of the tissue modification device.

Figure 1:
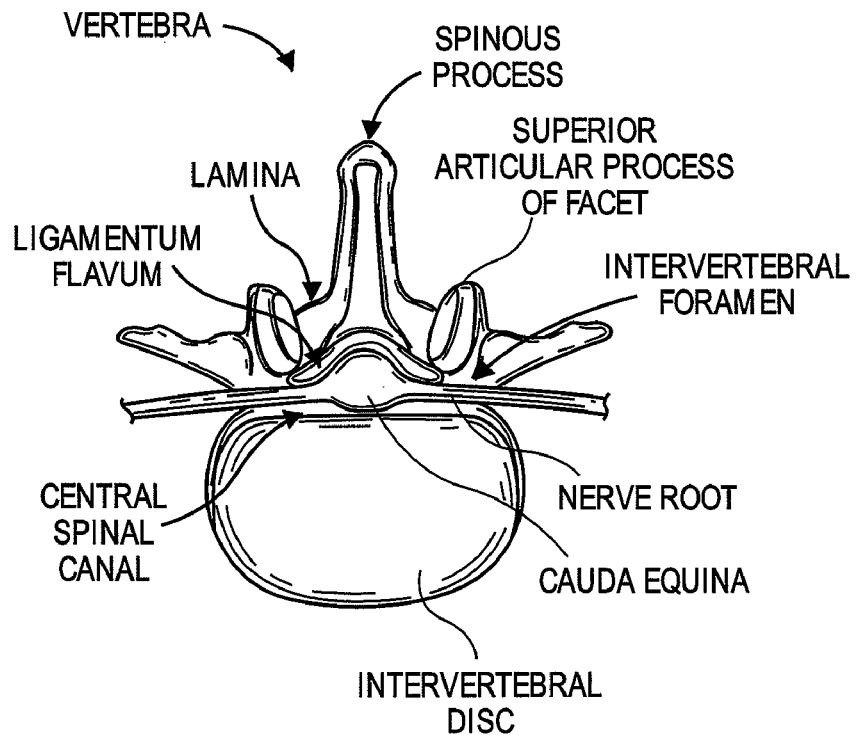
FIG. 1 is a cross section through the posterior aspect of the lumbar spine.
Figure 2:
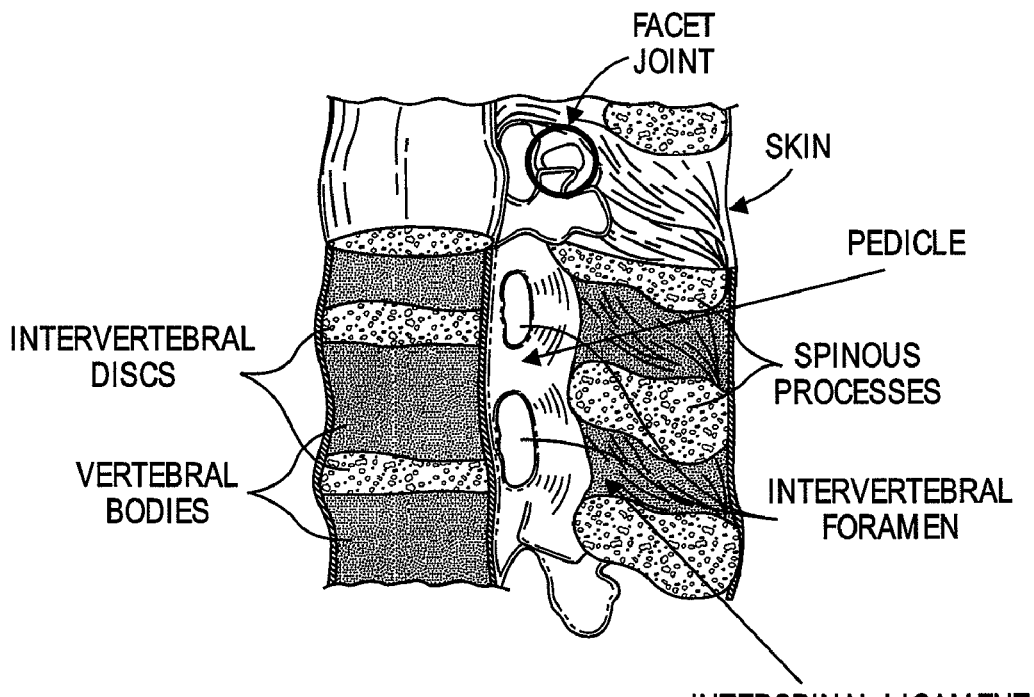
FIG. 2 is a sagittal section through the lumbar spine.
Figure 3A:
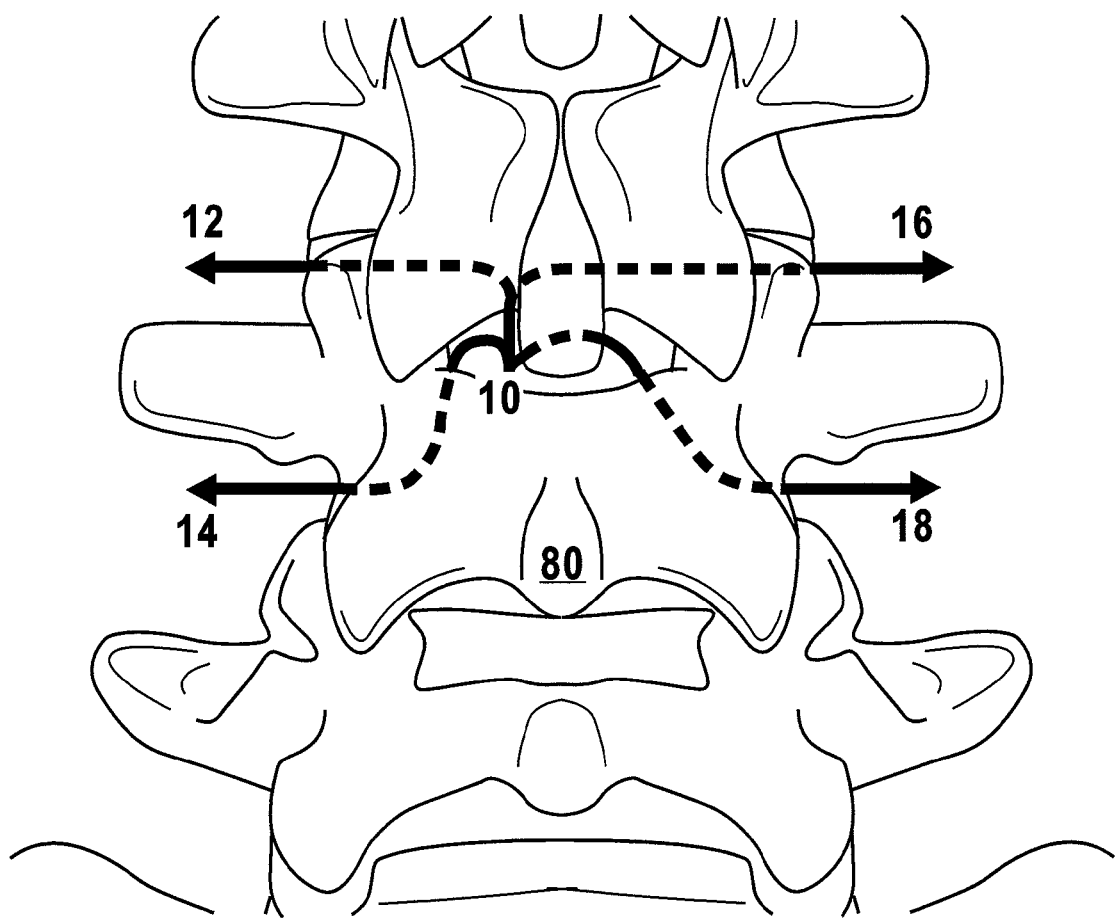
FIG. 3A is a posterior view of the spine indicating decompression paths at disk level and along the nerve root.
Figure 3B:
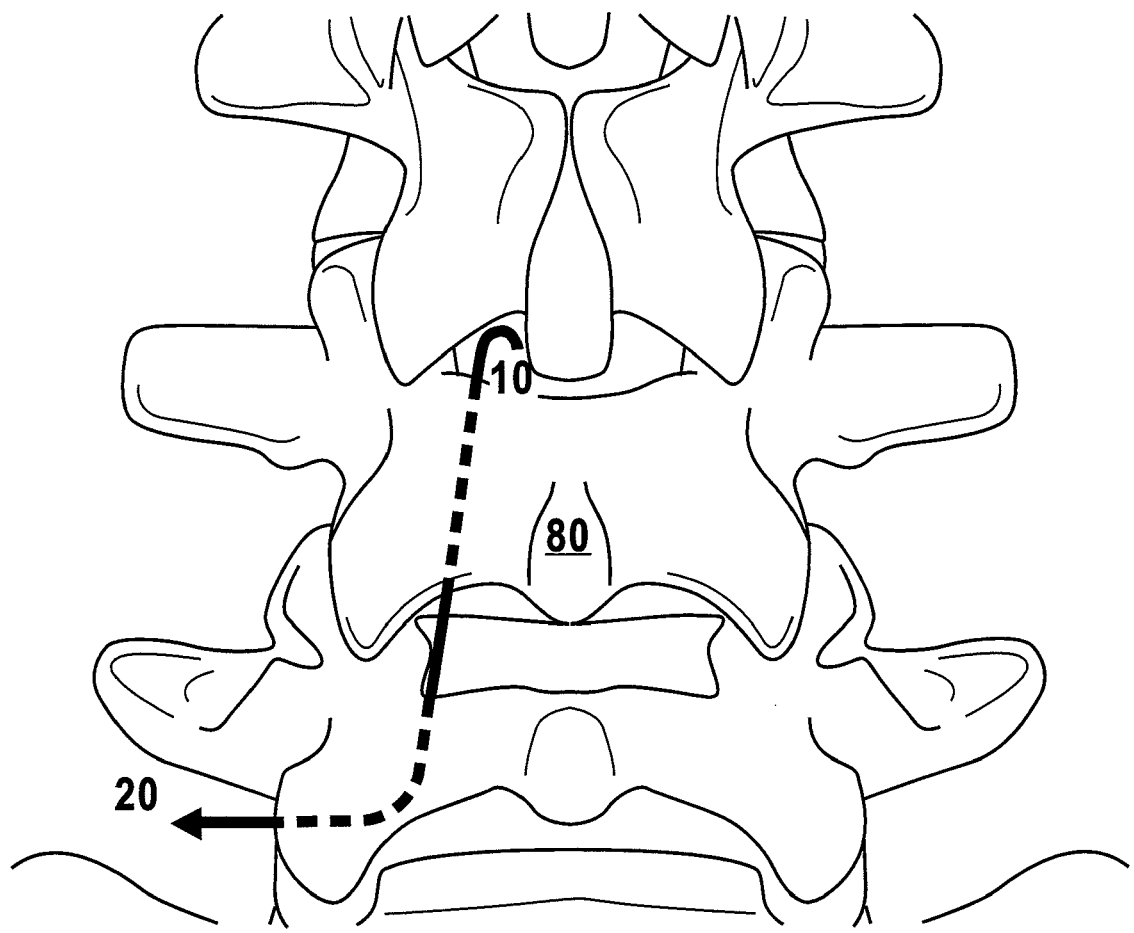
FIG. 3B is a posterior view of the spine indicating a decompression path for adjacent level lateral recess decompression.
Figure 3C:
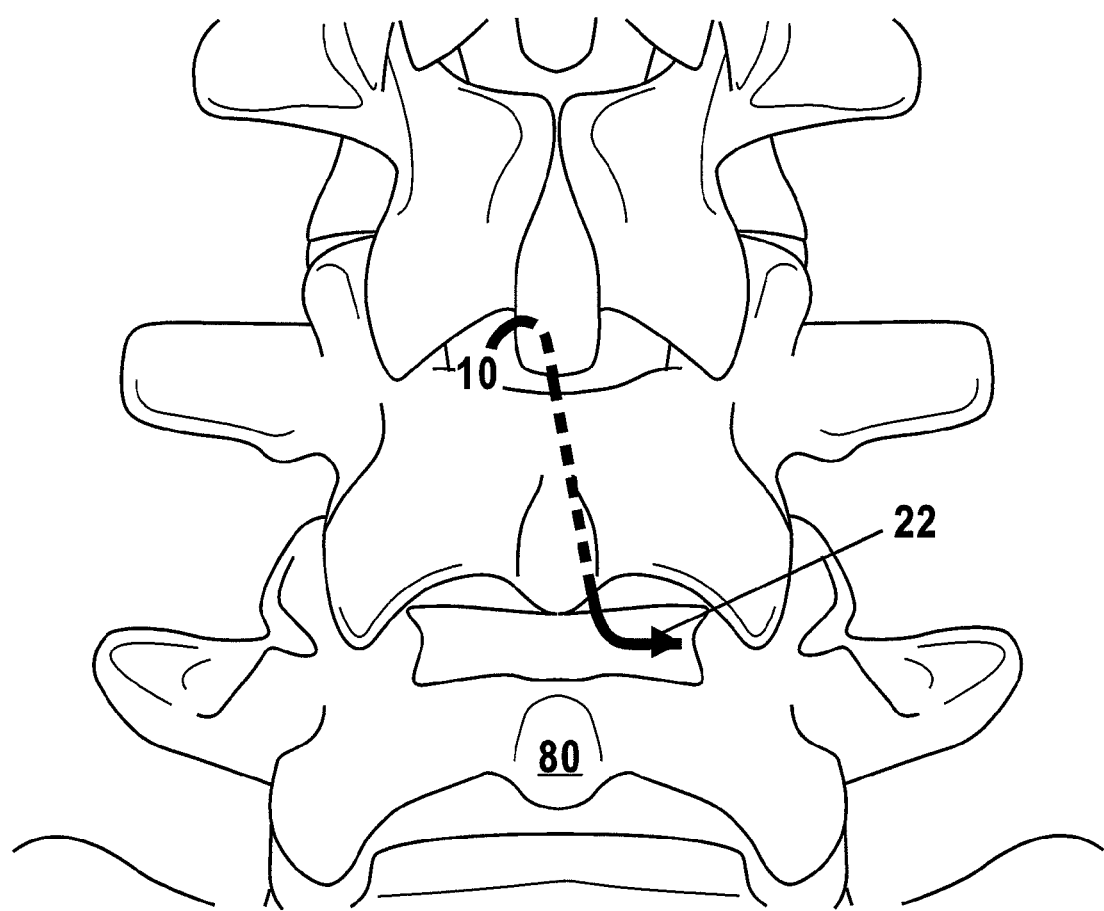
FIG. 3C is a posterior view of the spine indicating a decompression path for central canal decompression.

The step of advancing a distal portion of the first flexible tissue modification device from the spine location to a first exit location, further positions a tissue modification device such that it may be utilized to modify a target tissue. From the single access location, the tissue modification device may be advanced to one of several possible exit locations. As shown in FIG. 3A, from access location 10, the tissue modification device may be advanced to exit locations 12, 14, 16, 18, or any other suitable exit location. These exit locations may be through an intervertebral foramen. By advancing the tissue modification device from the spine location to exit location 12, the tissue modification device may be positioned to perform an ipsilateral disc level decompression (this may also be considered a lateral recess decompression). By advancing the tissue modification device from the spine location to exit location 14, the tissue modification device may be positioned to perform an ipsilateral decompression along the nerve root (this may also be considered a foraminal decompression). By advancing the tissue modification device from the spine location to exit location 16, the tissue modification device may be positioned to perform a contralateral disc level decompression. By advancing the tissue modification device from the spine location to exit location 18, the tissue modification device may be positioned to perform a contralateral decompression along the nerve root. As shown in FIG. 3B, from access location 10, the tissue modification device may be advanced to exit location 20. By advancing the tissue modification device from the spine location to exit location 20, the tissue modification device may be positioned to perform an ipsilateral adjacent level lateral recess decompression. The tissue modification device may alternatively be positioned to perform a contralateral adjacent level lateral recess decompression (not shown). As shown in FIG. 3C, from access location 10, the tissue modification device may be advanced to exit location 22. By advancing the tissue modification device from the spine location to exit location 22, the tissue modification device may be positioned to perform a central canal decompression.

Figure 8A:
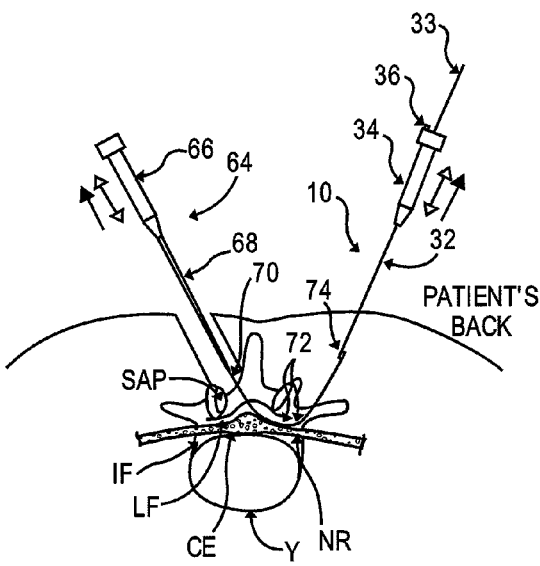
FIGS. 8A-8C are cross-sectional views through a patient's spine, illustrating variations of the tissue modification devices.

FIG. 8A illustrates a first variation of the step of advancing a distal portion of the first flexible tissue modification device. In this variation, the step of advancing a distal portion of the first flexible tissue modification device comprises advancing a guidewire from the spine location to the first or second exit location and pulling the flexible device around a target tissue using the guidewire. Guidewire 32 may be coupled to a distal portion of the tissue modification device. As shown in FIG. 8A, guidewire system 10 is shown with an embodiment of a tissue modification device 64, which may include a proximal handle 66, a rigid proximal shaft portion 68, and a distal flexible shaft portion 70. In this embodiment, guidewire 32 may be coupled with coupling member 74 and used to pull distal shaft portion 70 of modification device 64 into place between target and non-target tissues.

Figure 9A:
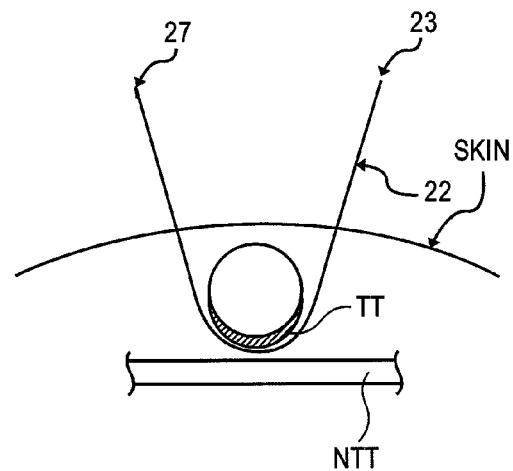
Figure 9B:
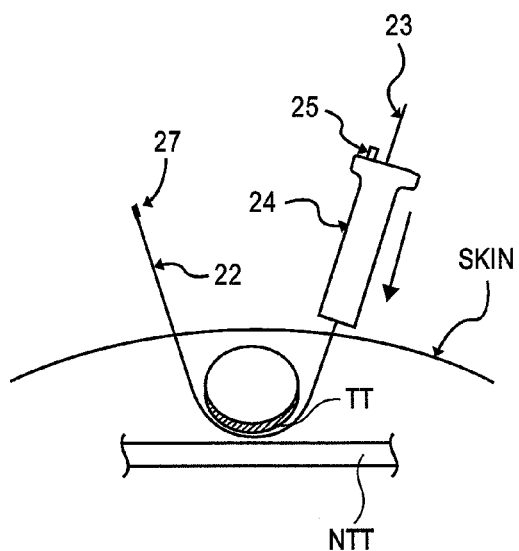
Figure 9C:
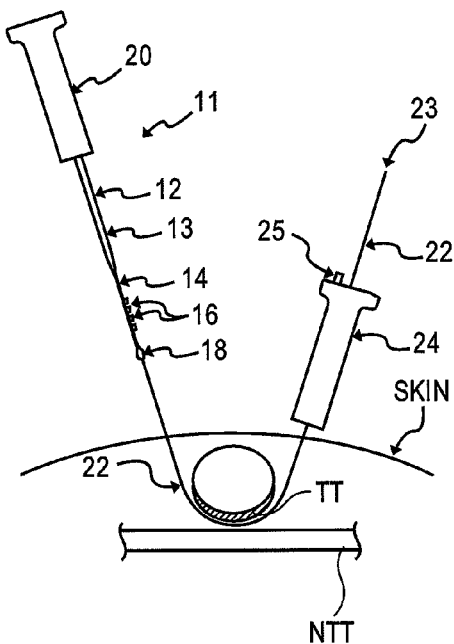

FIGS. 9D-9E illustrate a second variation of the step of advancing a distal portion of the first flexible tissue modification device. In this variation, the step of advancing a distal portion of the first flexible tissue modification device comprises pulling the tissue modification device into position by pulling on guidewire. Furthermore, the step of advancing the flexible device from the spine location to the exit location comprises positioning the flexible device at least partially around a target tissue. In some embodiments, positioning the flexible device at least partially around the target tissue comprises positioning the first or second flexible device anterior to a superior articular process and posterior to neuronal tissue, while in other embodiments, positioning the flexible device at least partially around the target tissue comprises positioning the flexible device within a portion of a ligamentum flavum, as shown in FIG. 10.

Referring to FIG. 9D, distal handle 24 may then be pulled (hollow-tipped arrow) to pull device 10 into the patient and to thus position tissue modifying members 16 in contact with target tissue TT. In some embodiments in which device 10 is used in the spine to treat spinal stenosis and/or neural or neurovascular impingement, device 10 may be passed into the patient and to a position for modifying tissue without removing any vertebral bone. More specifically, in some embodiments, device 10 may be advanced into the patient, through an intervertebral foramen, and out of the patient without removing bone. This is contrary to the majority of current surgical methods for treating spinal stenosis, which typically include removal of at least some vertebral bone, such as performing a laminotomy or laminectomy, and which often remove significant amounts of vertebral lamina, spinous process, facet and/or pedicle bony tissue, simply to access the surgical site. In one embodiment, for example, device 10 may be advanced percutaneously into the patient, used to remove ligamentum flavum only, and withdrawn from the patient, without removing any vertebral bone.

In a third variation, the tissue modification device may be advanced by pushing or pulling the modification device over a guidewire to the spine location. In this variation, the guidewire may function as a track or rail that the tissue modification device may be pushed or pulled over. In a fourth variation, the flexible tissue modification device may be advanced without the use of a guidewire. In this variation, the tissue modification device may be pushed to the desired location by pushing on a proximal handle and/or proximal end of the tissue modification device.

The step of passing through the first exit location and out of the patient, functions to bring a portion of a device out of the patient to offer a location for bimanual manipulation of the device. In some embodiments, the step of passing through the exit location and out of the patient comprises advancing through the intervertebral foramen and exiting the patient percutaneously with the guidewire, as shown in FIG. 4D. While the guidewire may exit the skin, the step of passing through a first or a second exit location may comprise leaving a proximal portion of the flexible tissue modification in the intervertebral foramen. As shown, guidewire 32 may be advanced through guide member 46 and out of the patient's back, using sharpened tip 33 to facilitate passage through the patient's back tissue. Probe 40 may then be removed, as shown in FIG. 4E, leaving guidewire 32 in place between the target and non-target tissues, as shown in FIG. 4F. Also shown in FIG. 4F is a shaped member 50 (in this embodiment, a ball) on the proximal end of guidewire 32. As described above, the shaped member is coupled to the flexible modification device such that the modification device can be pulled into position by the guidewire.

Figure 7C:
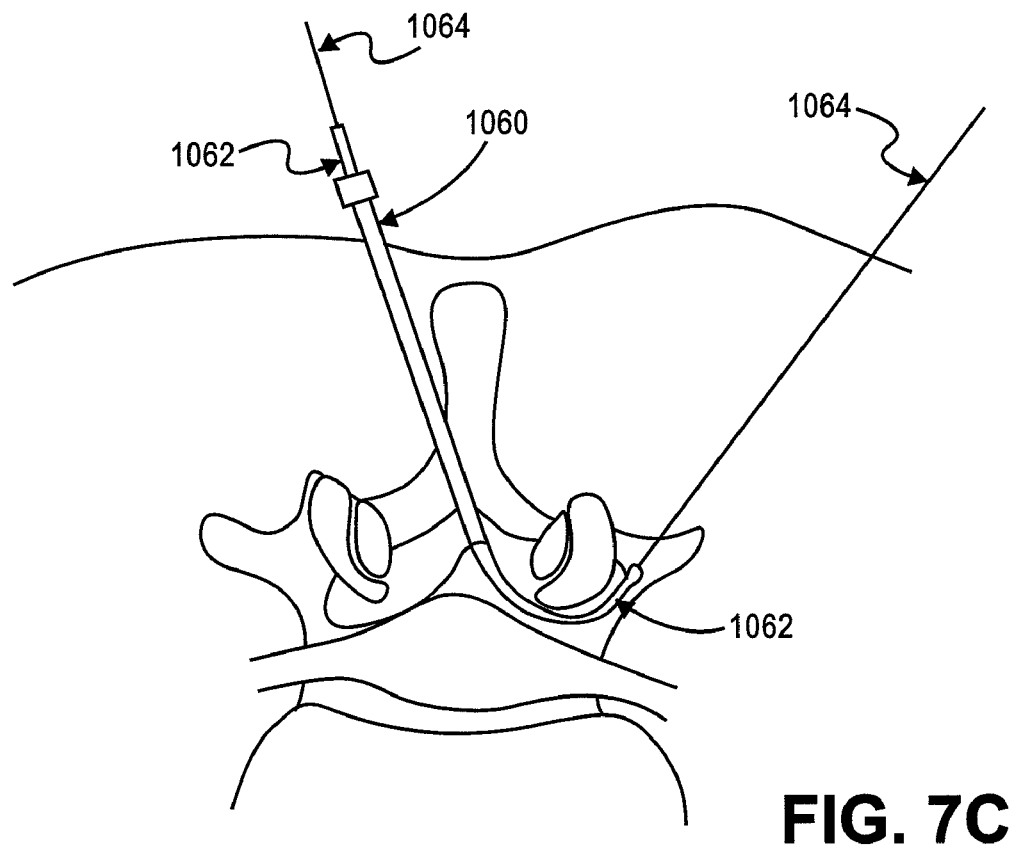
Figure 7D:
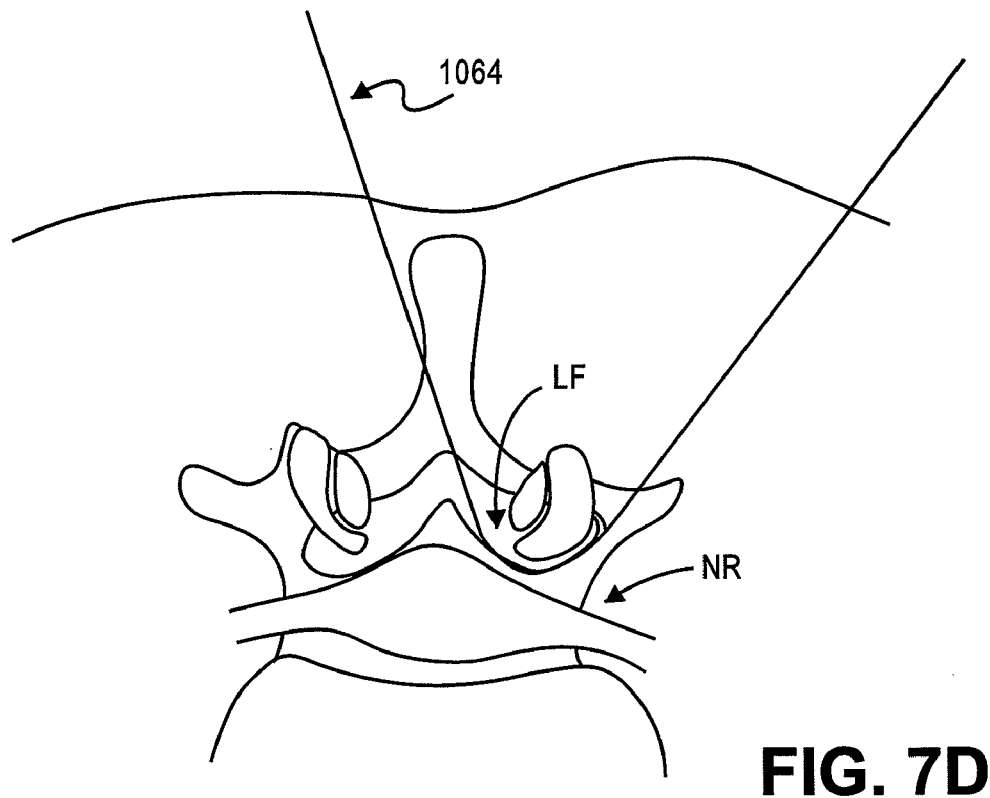

FIGS. 7C and 7D illustrate a second embodiment of the step of passing through the first exit location and out of the patient. As shown in FIG. 7C, nerve probe 1062 may include a guidewire lumen through which a guidewire may be passed, once it is determined that device 1062 is placed in a desired position between target and non-target tissue (e.g., avoiding a nerve adjacent to the upper region). As shown in FIG. 7D, when epidural needle 1060 and probe 1062 are removed, guidewire 1064 may be left in place between target tissue (such as ligamentum flavum LF and/or facet bone) and non-target tissue (such as cauda equina CE and nerve root NR). Any of a number of different minimally invasive or percutaneous surgical devices may then be pulled into the spine behind guidewire 1064 or advanced over guidewire 1064, such as the embodiment shown in FIG. 23 and others described by the assignee of the present application in other applications incorporated by reference herein.

The step of advancing the first or a second flexible tissue modification device through the same access location to the spine location and to a second exit location provides for decompressing a nerve root of the patient at second locations along the nerve root from the same access point as the first location decompressed. The same tissue modification device can be removed from the first exit location and reinserted back through the same access location to a second exit location, or alternatively, a second tissue modification device can be advanced through the same access location to a second exit location. The tissue modification devices may access several locations through any suitable path. For example, in a first variation, the step of advancing the flexible device from the spine location to the first exit location comprises advancing the first flexible device from the spine location, anterior to a superior articular process and cephalad to a pedicle, and through a intervertebral foramen (following arrow 12 in FIG. 3A). By following this path, the tissue modification device may be positioned posterior to and adjacent to a first nerve root. The step of advancing the flexible device from the spine location to the second exit location comprises advancing the flexible device from the spine location, anterior to a lamina and caudal to the pedicle, and through a second intervertebral foramen (following arrow 14 in FIG. 3A). By following this path, the tissue modification device may be positioned posterior to and adjacent to a second nerve root. For example, in a second variation, the step of advancing the flexible device from the spine location to a first exit location comprises advancing the first flexible device from the spine location, anterior to a superior articular process, and through a first intervertebral foramen (following arrow 12 in FIG. 3A), while the step of advancing the flexible device from the spine location to the second exit location comprises advancing the flexible device from the spine location, anterior to a superior articular process, and through a second intervertebral foramen (following arrow 16 in FIG. 3A).

The methods as described may further comprise the steps of inserting a flexible tissue modification device through the same access location to the spine location, and advancing the flexible tissue modification device from the spine location to a third exit location. Alternatively, any suitable number of tissue modification devices may be inserted through the same access location, and advanced along any suitable path within the spinal anatomy.

The methods as described may further comprise the steps of removing the first flexible tissue modification device from the patient and/or removing the second flexible tissue modification device from the patient. The tissue modification devices may be removed once the modification along the path through which they have been advanced is completed, alternatively, a first tissue modification device and a second tissue modification device may be in a patient, through the same access location, at the same time.

The methods as described may further comprise the steps of moving the flexible tissue modification device against the target tissue by pulling the flexible tissue modification device from at least one of the distal or proximal end of the tissue modification device and/or modifying the target tissue with the flexible tissue modification device. The target tissue along the path of the tissue modification device may be modified by the modification device by moving the device along the target tissue. As described above, in some embodiments, the tissue modification device may be pulled through and moved along the target tissue by pulling the device from one end by a guidewire, or alternatively by pulling the device over the guidewire. In some embodiments, the step of moving the flexible tissue modification device against a target tissue by pulling the flexible tissue modification device from at least one of the distal or proximal end of the device comprises applying tension to both the proximal end and the distal end of the flexible tissue modification device to drive the flexible device against the target tissue.

FIG. 8A illustrates a first variation of the step of applying tension to both the proximal end and the distal end of the flexible tissue modification device. As shown, proximal handle 66 and distal handle 34 may be pulled/tensioned (solid-tipped arrows) to urge abrasive members 72 against the target tissue, and handles 66, 34 may further be used to reciprocate device 64 and guidewire 32 back and forth (hollow/double-tipped arrows) to modify the target tissue. Reciprocation and tensioning may be continued until a desired amount of tissue is removed, at which point guidewire 32 may be released from distal handle 34, and device 64 and guidewire 32 may be removed from the patient's back. In various embodiments, tissue modification device 64 may include any of a number of abrasive members 72, abrasive materials, or the like, which may be arrayed along distal shaft portion 70 for any desired length and in any desired configuration.

FIG. 9E illustrates a second variation of the step of applying tension to both the proximal end and the distal end of the flexible tissue modification device. As shown in FIG. 9E, once tissue modifying members 16 are positioned as desired, relative to target tissue TT, proximal handle 20 and guidewire handle 24 may be pulled (hollow-tipped arrows) to urge tissue modifying members 16 against target tissue TT (solid-tipped, single-headed arrows). While maintaining pulling/tensioning force, handles 20, 24 may be used to reciprocate device 10 back and forth (solid-tipped, double-headed arrows) to remove target tissue TT. When a desired amount of tissue is removed, device 10 may be removed from the patient, such as by detaching guidewire handle 24 from guidewire 22 and pulling proximal handle 20 to withdraw device 10 and guidewire 22 out of the patient. Device 10 or an additional device may be reinserted into the patient and used in a second location to remove additional tissue. For example, in a spinal stenosis treatment procedure, device 10 may be used to remove tissue from (and thus decompress) a first intervertebral foramen and then may be removed and reinserted to remove tissue from a second foramen. This process may be repeated to remove tissue from any number of foramina. In one embodiment, device 10 may include a guidewire lumen, so that a guidewire may be placed into a second foramen while device 10 is in the epidural space of the patient. Device 10 may then be removed along with the first guidewire 22, attached to the second guidewire, and reinserted into the second foramen to remove tissue. In some embodiments, tissue may be removed from device 10 before reinserting device 10 into the patient to remove more tissue.

The methods as described may further comprise the step of detecting neuronal tissue near the flexible tissue modification device. This step may be performed to ensure that the tissue modification device is positioned such that the neuronal tissue; such as the nerve root, or the dura mater of the spinal cord and cauda equina; will not be modified by the tissue modification device. The tissue modification device may include at least one electrode to locate the position of the detecting neuronal tissue or alternatively, a separate device may be inserted and advanced into location.

Figure 5B:
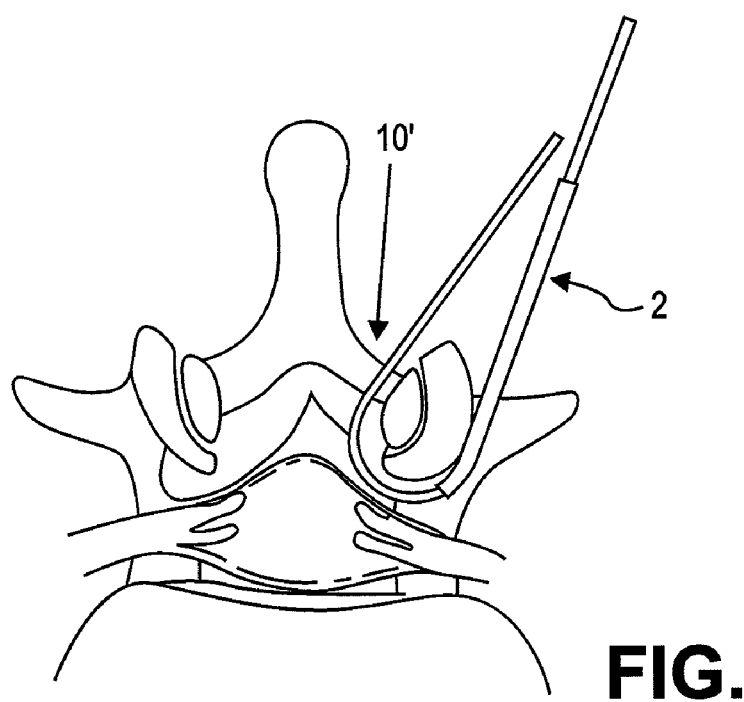

In some embodiments, as shown in FIG. 5A, the method of accessing target tissue adjacent to a spinal nerve of a patient may alternatively include the steps of accessing a spine location 100 of the patient by entering the patient through the skin at a first access location; inserting a flexible tissue modification device 102 through the first access location 12' to the spine location 100; advancing a distal portion of the first flexible tissue modification device from the spine location to an exit location 10', as shown in FIG. 5B; passing out of the patient through the first exit location; advancing the first or a second flexible tissue modification device through the same access location to the spine location and to a second exit location; and passing through the second exit location and out of the patient. The spine location may be anterior to the posterior aspect of the ligamentum flavum LF and posterior to the dura mater of the spinal cord and cauda equina CE. In some embodiments, as shown in FIG. 4A, the spine location may be the epidural space. The methods are designed for accessing target tissue, and more specifically, for accessing and decompressing a spinal stenosis. The methods however, may be alternatively used for any other suitable disease, in any suitable environment and for any suitable reason.

Tissue Modification Devices

As described, the tissue modification devices typically include a flexible elongate body that extends proximally to distally (proximal/distal), and is configured to be inserted into a patient so that it extends around the target tissue, so that it can be bimanually pulled against the target tissue by applying tension to either end of the device. Thus, the device may be extended into and through and around a spinal foramen. The device is flexible in at least one plane. For example, in variations in which the device has an elongated ribbon shape that is long and flat with a width greater than the thickness, the device includes a first major surface (e.g., a front) and a second major surface (a back), and has edges (minor surfaces) connecting the first and second major surfaces. The first major surface may be referred to as the anterior or front surface and the second major surface may be referred to as the posterior or back surface. The devices described herein may be flexible along the anterior and posterior surfaces, and the anterior or front surface may include one or more cutting edges configured to cut tissue as the anterior surface of the device is urged against a tissue. The posterior surface may be configured to shield or protect non-target tissue.

Figure 11:
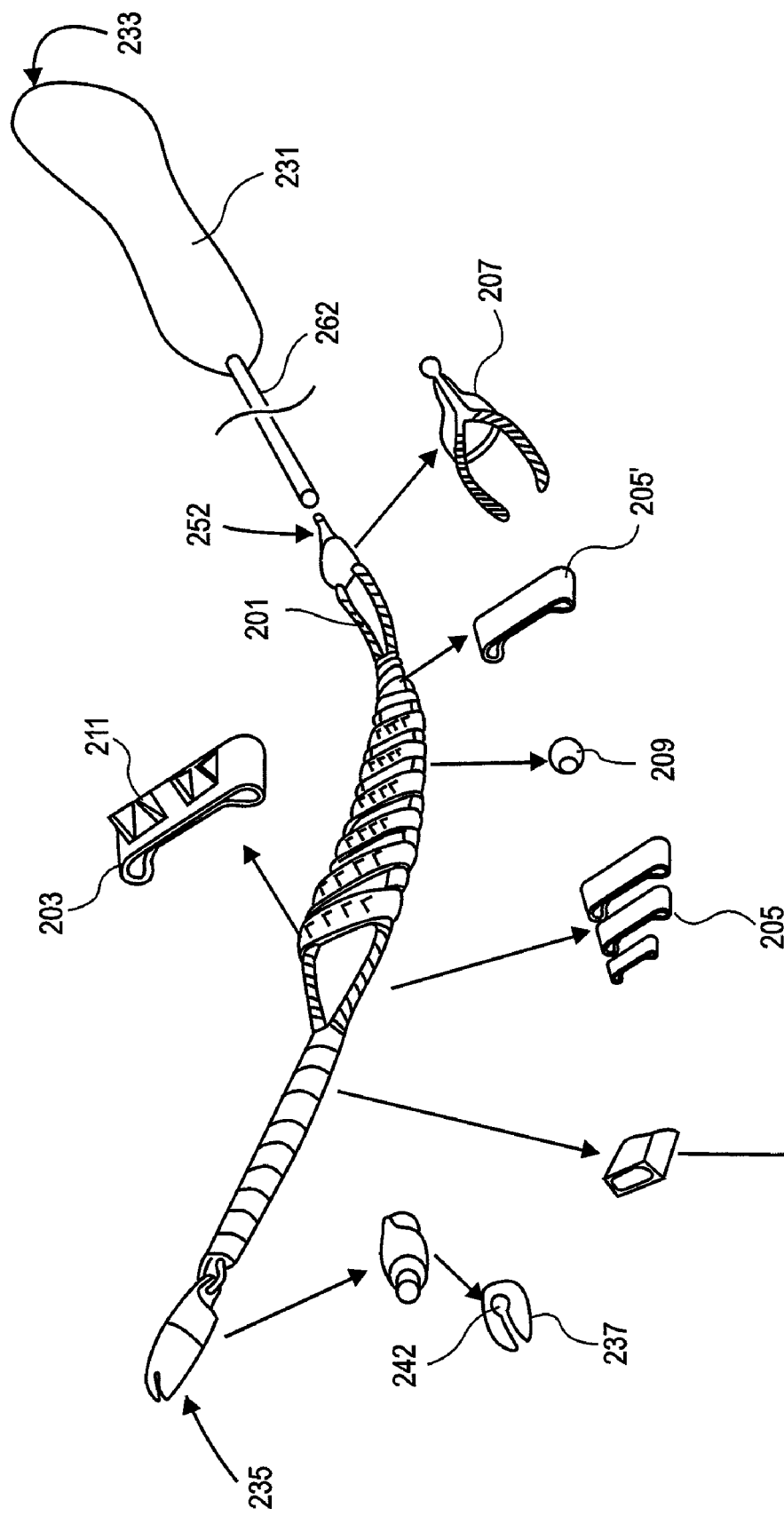
FIG. 11 is a drawing of a variation of a tissue modification device.

For example, as shown in FIG. 11 in some embodiments, the tissue modification devices typically include one or more of the following features: all or a portion of the device maybe formed of flexibly connected rungs or links; the devices may include a tissue capture region having a fixed minimum volume; and the device may be configured so that the major/minor surfaces may have non-linear shapes along their length, or may be stitched between linear and non-linear shapes. A tissue modification device may include one or more of these features in any combination. Each of these features is described and illustrated in greater detail below.

As shown in FIG. 8A, an embodiment of a tissue modification device 64 may include a proximal handle 66, a rigid proximal shaft portion 68, and a distal flexible shaft portion 70. Multiple abrasive members 72 and a guidewire coupling member 74 may be coupled with one side of flexible shaft portion 70. Proximal handle 66 and distal handle 34 may then be pulled/tensioned (solid-tipped arrows) to urge abrasive members 72 against the target tissue, and handles 66, 34 may further be used to reciprocate device 64 and guidewire 32 back and forth (hollow/double-tipped arrows) to modify the target tissue. Reciprocation and tensioning may be continued until a desired amount of tissue is removed, at which point guidewire 32 may be released from distal handle 34, and device 64 and guidewire 32 may be removed from the patient's back. In various embodiments, tissue modification device 64 may include any of a number of abrasive members 72, abrasive materials, or the like, which may be arrayed along distal shaft portion 70 for any desired length and in any desired configuration. Further examples of abrasive members 70, materials, surfaces and the like are described in U.S. patent application Ser. No. 11/429,377, which was previously incorporated by reference. In various alternative embodiments, shaft portions 68, 70 may both be rigid or may both be flexible and may have different cross-sectional shapes or the same shape.

Figure 8B:
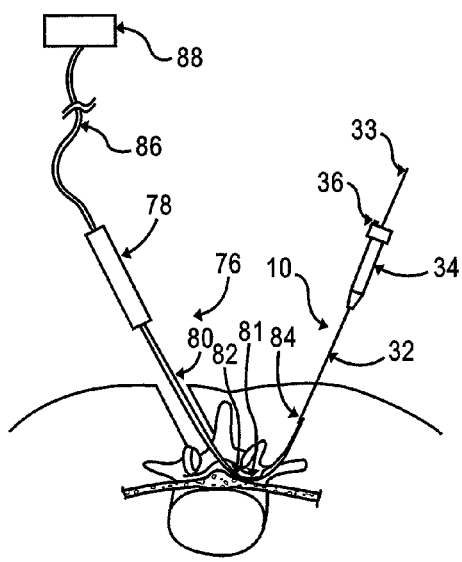

As shown in FIG. 8B, an alternative embodiment of the tissue modification device is an ultrasound tissue modification device 76 that may also be advanced into position in a patient's back using guidewire system 10. In one embodiment, for example, ultrasound device 76 may include a proximal handle 78, a hollow shaft 80 having a distal window 81, multiple ultrasound wires 82 extending through shaft 80 and into window 81, a guidewire connector 84 coupled with a tapered distal end of shaft 80, an ultrasound generator 88, and a wire 86 coupling handle 78 with generator 88. Handle 78 may include, for example, an ultrasound transducer, horn and/or other ultrasound transmission components. Shaft 80 may be completely rigid, completely flexible, or part rigid/part flexible, according to various embodiments. Ultrasound energy provided by generator 88 may be converted in handle 78 to reciprocating motion of wires 82, and reciprocating wires 82 may be used to cut, chisel or otherwise modify soft and/or hard tissues. Further description of such an embodiment is provided in U.S. patent application Ser. No. 11/461,740, which was previously incorporated by reference. Guidewire connector 84 may comprise one of a number of different connectors, various embodiments of which are described in further detail below.

Figure 8C:
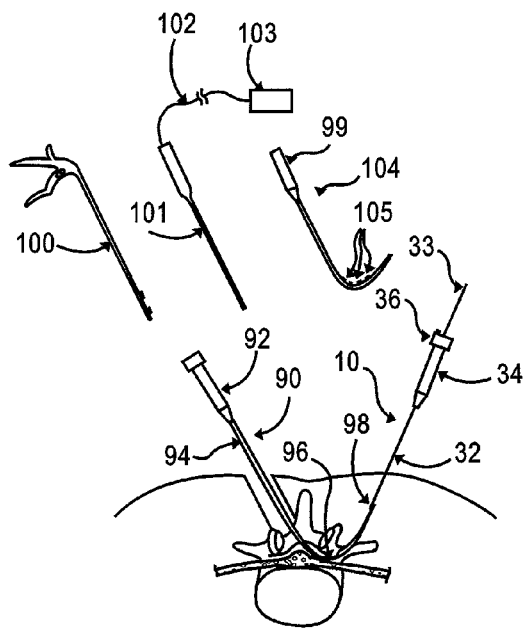

In another embodiment, and with reference now to FIG. 8C, guidewire system 10 may be used to pull/advance a tissue access device 90 into place between target and non-target tissues. Tissue access device 90, for example, may include a proximal handle 92, a hollow shaft 94 having a distal curved portion with a distal window 96, and a guidewire connector 98 coupled with a tapered distal end of shaft 94. As with previously described embodiments, shaft 94 may be flexible along its entire length, rigid along its entire length, or rigid in part and flexible in part, and may be made of any suitable material or combination of materials. In some embodiments, shaft 94 may also be steerable, such as with one or more pull wires or other steering mechanisms, for example to steer or curve a distal portion of shaft 94.

Once access device 90 is in a desired position, with window 96 facing target tissue (such as ligamentum flavum and/or facet joint bone in the spine) and an atraumatic surface of shaft 94 facing non-target tissue, any of a number of compatible tissue modification devices 100, 101, 104 or other devices may be advanced through access device 90 to perform a tissue modification procedure or other functions. Such devices may swappable in and out of access device 90 and may be in the form of cartridges, so that various cartridges may be inserted and removed as desired, over the course of a procedure. Examples of several tissue modification devices are shown in FIG. 8A, including a rongeur device 100, an ultrasound device 101 (including wire 102 and ultrasound generator 103), and an abrasive, reciprocating device 104. Further examples of tissue modification and other devices are described below with reference to FIGS. 8B-8M.

In one embodiment, for example, at least a distal portion of each tissue modification device 100, 101, 104 may be flexible, and a proximal portion of each modification device 100, 101, 104 may have a locking feature for locking into proximal handle 92 of access device 90. Thus, a given modification device, such as abrasive device 104, may be advanced into handle 92 and shaft 94, so that abrasive members 105 of device 104 are exposed through window 96 and locking feature 99 of device couples and locks within handle 92. A user may then grasp handles 34 and 92, pull up to urge abrasive members 105 against target tissue, and reciprocate access device 90 and guidewire system 10 back and forth to remove target tissue. The user may then choose to remove abrasive device 104 and insert one of the other devices 100, 101 to further modify target tissues.

In various embodiments, any of a number of tissue modification devices and/or other devices may be provided (for example as cartridges) for used with access device 90. In some embodiments, one or more of such devices may be provided with access device 90 and guidewire device 10 as a system or kit. Any given tissue modification device may act on tissue in a number of different ways, such as by cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting target tissue. Non-tissue-modifying devices or cartridges may additionally or alternatively be provided, such as but not limited to devices for: capturing, storing and/or removing tissue; delivering a material such as bone wax or a pharmacologic agent such as thrombin, NSAID, local anesthetic or opioid; delivering an implant; placing a rivet, staple or similar device for retracting tissue; delivering a tissue dressing; cooling or freezing tissue for analgesia or to change the tissue's modulus of elasticity to facilitate tissue modification; visualizing tissue; and/or diagnosing, such as by using ultrasound, MRI, reflectance spectroscopy or the like. In given method, system or kit, any combination of tissue modification and/or non-tissue-modifying devices may be used with access device 90. In some embodiments, the tissue modification device may be a radio-frequency device, which in some embodiments heats, ablates, and/or shrinks the target tissue.

Although preferred illustrative embodiments are described herein, it will be apparent to those skilled in the art that various changes and modifications may be made thereto without departing from the invention. It is intended in the appended claims to cover all such changes and modifications that fall within the true spirit and scope of the invention.

What is claimed is:

1. A method of accessing target tissue adjacent to a spinal nerve of a patient, comprising:
    accessing a spine location of the patient through the skin at an access location that is anterior to the posterior aspect of the ligamentum flavum and posterior to the dura mater of the spinal cord and cauda equina;

inserting a first flexible tissue modification device through the access location to the spine location;

advancing a distal portion of the first flexible tissue modification device from the spine location to a first exit location;

passing through the first exit location and out of the patient;

advancing the first or a second flexible tissue modification device through the same access location to the spine location and to a second exit location;

passing through the second exit location and positioning the first or second flexible device at least partially around a target tissue;

passing through the second exit location and out of the patient;

moving the first or second flexible device against the target tissue by pulling the first or second flexible device from at least one of the distal or proximal end of the first or second flexible device; and modifying the target tissue with the first or second flexible device.

2. The method of claim 1, further comprising the step of removing the first flexible tissue modification device from the patient.

3. The method of claim 2, further comprising the step of removing the second flexible tissue modification device from the patient.

4. The method of claim 1, wherein the step of advancing the first or the second flexible tissue modification device to a first or second exit location comprises advancing the first or the second flexible tissue modification device to a first or second intervertebral foramen.

5. The method of claim 4, wherein the step of passing through a first or a second exit location comprises leaving a proximal portion of the first or the second flexible tissue modification in the first or second intervertebral foramen.

6. The method of claim 1, further comprising the steps of:
inserting the first, the second, or a third flexible device through the same access location to the spine location; and
advancing the first, the second or the third flexible device from the spine location to a third exit location.

7. The method of claim 1, wherein first exit location and the second exit location are ipsilateral to the access location.

8. The method of claim 1, wherein first exit location is ipsilateral to the access location and the second exit location is contralateral to the access location.

9. The method of claim 1, wherein first exit location and the second exit location are cephalad to the access location.

10. The method of claim 1, wherein first exit location is cephalad to the access location and the second exit location is caudal to the access location.

11. The method of claim 1, wherein the step of accessing a spine location of the patient through an access location comprises accessing a spine location of the patient through an interlaminar window of the patient.

12. The method of claim 11, wherein the step of accessing a spine location of the patient through an interlaminar window is achieved without removing a portion of the patient's lamina.

13. The method of claim 1, wherein the step of accessing a spine location of the patient through an access location comprises advancing an access device through the access location to the spine location.

14. The method of claim 13, wherein the step of advancing the access device through the access location to the spine location comprises advancing the access device into a midline portion of the back of the patient, lateral to a spinous process, and toward the spine location.

15. The method of claim 13, wherein the step of advancing an access device through the access location to the spine location comprises advancing a needle percutaneously through the access location to the spine location.

16. The method of claim 13, wherein the step of advancing an access device through the access location to the spine location comprises advancing the access device into a lateral side of the back of the patient, through an intervertebral foramen, and toward the spine location.

17. The method of claim 13, wherein the step of advancing the first flexible device from the spine location to the first exit location comprises advancing at least a portion of a probe through the access device from the spine location toward the first exit location, and advancing a guidewire through the probe such that the guidewire is positioned at least partially around a target tissue.

18. The method of claim 17, wherein the step of passing through the first or second exit location and out of the patient comprises advancing the guidewire through the first or second exit location and exiting the patient with the guidewire.

19. The method of claim 1, wherein the step of advancing the first flexible device from the spine location to a first exit location comprises advancing the first flexible device from the spine location, anterior to a superior articular process, and through a first intervertebral foramen; and wherein the step of advancing the first or the second flexible device from the spine location to the second exit location comprises advancing the first or second flexible device from the spine location, anterior to a superior articular process, and through a second intervertebral foramen.

20. The method of claim 1, wherein the step of advancing the first flexible device from the spine location to the first exit location comprises advancing the first flexible device from the spine location, anterior to a superior articular process and cephalad to a pedicle, and through a intervertebral foramen; and wherein the step of advancing the first or second flexible device from the spine location to the second exit location comprises advancing the first or second flexible device from the spine location, anterior to a lamina and caudal to the pedicle, and through a second intervertebral foramen.

21. The method of claim 1, wherein the step of advancing the first or second flexible device from the spine location to the first or second exit location comprises advancing a guidewire from the spine location to the first or second exit location and pulling the flexible device around a target tissue using the guidewire.

22. The method of claim 21, wherein the step of passing through the first or second exit location and out of the patient comprises advancing through the first or second intervertebral foramen and exiting the patient percutaneously with the guidewire.

23. The method of claim 1, wherein the step of positioning the first or second flexible device at least partially around the target tissue comprises positioning the first or second flexible device anterior to a superior articular process and posterior to neuronal tissue.

24. The method of claim 23, wherein the step of positioning the first or second flexible device at least partially around the target tissue comprises positioning the flexible device within a portion of a ligamentum flavum.

25. The method of claim 1, wherein the step of moving the first or second flexible device against a target tissue by pulling the first or second flexible device from at least one of the distal or proximal end of the device comprises applying tension to both the proximal end and the distal end of the first or second flexible device to drive the flexible device against the target tissue.

26. The method of claim 25, wherein the step of advancing the first or second flexible device from the spine location to a first or second exit location comprises advancing a guidewire from the spine location to the first or second exit location, advancing the guidewire through the first or second exit location to exit the patient, and pulling the first or second flexible device around a target tissue using the guidewire.

27. The method of claim 25, wherein the step of applying tension to both the proximal end and the distal end of the first or second flexible device to drive the first or second flexible device against the target tissue comprises applying tension to the distal end of the first or second flexible device using the guidewire.

28. The method of claim 25, wherein applying tension to the distal end of the first or second flexible device using the guidewire comprises applying tension to the distal end of the guidewire external to the patient and a proximal end of the guidewire external to the patient.

29. The method of claim 1, wherein the step of modifying a target tissue with the first or second flexible device comprises modifying the target tissue with a flexible radio-frequency device.

30. The method of claim 1, wherein the step of modifying a target tissue with a first or second flexible device comprises modifying the target tissue with a flexible abrasion device.

31. The method of claim 1, wherein the step of modifying a target tissue with the flexible device comprises modifying the target tissue with a flexible rongeur device.

32. The method of claim 1, further comprising the step of detecting neuronal tissue near the first or second flexible device.

33. The method of claim 32, wherein the step of detecting neuronal tissue near the first or second flexible device comprises detecting neuronal tissue with the first or second flexible device.

34. A method of accessing target tissue adjacent to a spinal nerve of a patient, the method comprising:
  accessing a spine location of the patient by entering the patient through an access location, wherein the spine location is anterior to the posterior aspect of the ligamentum flavum and posterior to the dura mater of the spinal cord and cauda equina, and the access location is lateral to the spinous process;
  inserting a first flexible device through the access location, through the interlaminar window, and to the spine location;
  advancing a distal portion of the first flexible device from the spine location, laterally through a first intervertebral foramen;
  passing through the first intervertebral foramen and out of the patient;
  inserting the first or a second flexible device through the same access location, through the interlaminar window, and to the spine location; and
  advancing a distal portion of the first or second flexible device from the spine location and laterally through a second intervertebral foramen and positioning the first or second flexible device at least partially around a target tissue;
  passing through the second intervertebral foramen and out of the patient;
  moving the first or second flexible device against the target tissue by pulling the first or second flexible device from at least one of the distal or proximal end of the first or second flexible device; and
  modifying the target tissue with the first or second flexible device.

35. The method of claim 34, wherein the step of inserting the first or second flexible device through the access location, through the interlaminar window, and to the spine location is achieved without removing a portion of the patient's lamina.

36. The method of claim 34, wherein the step of advancing the first flexible device from the spine location and laterally through a first intervertebral foramen comprises advancing the first flexible device anterior to the ipsilateral superior articular process.

37. The method of claim 36, wherein the step of advancing the first flexible device from the spine location and laterally through a first intervertebral foramen comprises positioning the first flexible device posterior to and adjacent to a first nerve root, wherein the first nerve root exits through the first intervertebral foramen, wherein the first intervertebral foramen is defined by the same vertebra that define the interlaminar window.

38. The method of claim 37, wherein the step of positioning the first flexible device posterior to the first nerve root comprises positioning the first flexible device posterior to and adjacent to the exiting portion of the first nerve root.

39. The method of claim 34, wherein the step of advancing the first or second flexible device from the spine location and laterally through a second intervertebral foramen comprises advancing the first or second flexible device anterior to the lamina.

40. The method of claim 39, wherein the step of advancing the first or second flexible device from the spine location and laterally through a second intervertebral foramen comprises positioning the flexible device posterior to and adjacent to a second nerve root, wherein the second nerve root exits through the second intervertebral foramen, wherein the second intervertebral foramen is caudal to the first intervertebral foramen.

41. The method of claim 40, wherein the step of positioning the first or second flexible device posterior to the second nerve root comprises positioning the first or second flexible device posterior to and adjacent to the traversing portion of the second nerve root.

42. The method of claim 34, wherein the step of advancing the first flexible device from the spine location and laterally through a first intervertebral foramen comprises advancing the first flexible device anterior to a contralateral superior articular process and through a contralateral intervertebral foramen, wherein the contralateral superior articular process and the contralateral intervertebral foramen are contralateral to the access location.

43. The method of claim 34, wherein the step of advancing the first or second flexible device from the spine location, laterally through the second intervertebral foramen comprises advancing the flexible device anterior to the lamina, and through the caudal intervertebral foramen, wherein the lamina and the caudal intervertebral foramen are contralateral to the access location and the caudal intervertebral foramen is caudal to the first intervertebral foramen.

44. The method of claim 34, wherein the step of advancing the first or second flexible device from the spine location and laterally through the first or second intervertebral foramen comprises positioning the first or second flexible device at least partially around a target tissue.

45. The method of claim 44, wherein the step of positioning the first or second flexible device at least partially around the target tissue comprises positioning the first or second flexible device between within a portion of a ligamentum flavum.

46. The method of claim 34, wherein the steps of modifying the target tissue with the first or second flexible device comprises decompressing a nerve root of the patient at multiple locations along the nerve root.

47. The method of claim 46, wherein decompressing the nerve root of the patient at multiple locations along the nerve root comprises decompressing the nerve root at least two of a central canal, a lateral recess, and through the first or second intervertebral foramen.

48. A method of accessing target tissue adjacent to a spinal nerve of a patient, comprising:
   accessing a spine location of the patient through the skin at an access location that is anterior to the posterior aspect of the ligamentum flavum and posterior to the dura mater of the spinal cord and cauda equina;
   inserting a first flexible tissue modification device through the access location to the spine location;
   advancing a distal portion of the first flexible tissue modification device from the spine location to a first exit location;
   passing through the first exit location and out of the patient;
   advancing the first or a second flexible tissue modification device through the same access location to the spine location and to a second exit location;
   passing through the second exit location and out of the patient; and
   detecting neuronal tissue near the first or second flexible device.

49. A method of accessing target tissue adjacent to a spinal nerve of a patient, comprising:
   accessing a spine location of the patient through the skin at an access location that is anterior to the posterior aspect of the ligamentum flavum and posterior to the dura mater of the spinal cord and cauda equina;
   inserting a first flexible tissue modification device through the access location to the spine location;
   advancing a distal portion of the first flexible tissue modification device from the spine location to a first exit location;
   passing through the first exit location and out of the patient;
   advancing the first flexible tissue modification device through the same access location to the spine location and to a second exit location; and
   passing through the second exit location and out of the patient.

* * * * *